(12) United States Patent
Melnick et al.

(10) Patent No.: US 8,791,075 B2
(45) Date of Patent: Jul. 29, 2014

(54) METHODS AND COMPOSITIONS FOR INHIBITION OF BCL6 REPRESSION

(75) Inventors: Ari Melnick, New York, NY (US); Leandro Cerchietti, New York, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 324 days.

(21) Appl. No.: 12/737,122

(22) PCT Filed: Jun. 10, 2009

(86) PCT No.: PCT/US2009/003483
§ 371 (c)(1),
(2), (4) Date: Mar. 4, 2011

(87) PCT Pub. No.: WO2010/008436
PCT Pub. Date: Jan. 21, 2010

(65) Prior Publication Data
US 2011/0152200 A1    Jun. 23, 2011

Related U.S. Application Data

(60) Provisional application No. 61/132,948, filed on Jun. 24, 2008.

(51) Int. Cl.
| | | |
|---|---|---|
| *A61K 38/04* | (2006.01) | |
| *A61K 38/08* | (2006.01) | |
| *A61K 38/00* | (2006.01) | |
| *C07K 7/06* | (2006.01) | |
| *C07K 7/00* | (2006.01) | |
| *A61K 47/48* | (2006.01) | |

(52) U.S. Cl.
CPC ... *C07K 7/06* (2013.01); *C07K 7/00* (2013.01); C07K 2319/00 (2013.01); C07K 2319/10 (2013.01); *A61K 38/04* (2013.01); *A61K 38/08* (2013.01); *A61K 38/00* (2013.01); A61K 47/48315 (2013.01)
USPC ........ 514/19.3; 514/19.4; 514/21.6; 530/300; 530/328

(58) Field of Classification Search
CPC ....... A61K 38/04; A61K 38/08; A61K 38/00; A61K 47/48315; C07K 7/06; C07K 7/00; C07K 2319/00; C07K 2319/10
USPC ................ 514/19.3, 19.4, 21.6; 530/300, 328
See application file for complete search history.

(56) References Cited

U.S. PATENT DOCUMENTS

| | | | | |
|---|---|---|---|---|
| 5,595,756 A | * | 1/1997 | Bally et al. | 424/450 |
| 2009/0018083 A1 | | 1/2009 | Melnick et al. | |
| 2010/0130564 A1 | | 5/2010 | Melnick et al. | |

FOREIGN PATENT DOCUMENTS

WO    WO 2005/058939 A2    6/2005

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*
Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Cancer Drug Design and Discovery Neidle, Stephen, ed. (Elsevier/Academic Press, 2008) pp. 427-431.*
Polo J M et al., entitled "Specific peptide interference reveals BCL6 transcriptional and oncogenic mechanisms in B-cell lymphoma cells," Nature Medicine Advance Online, Nov. 7, 2004 at http://xtal.oci.utoronto.ca/prive/2004_Polo_BCL6.pdf, pp-1-7.
Ahmad K F et al., entitled "Mechanism of SMRT Corepressor Recruitment by the BCL6 BTB Domain," Molecular Cell, vol. 12, 1551-1564, Dec. 2003, pp. 1551-1564.
Ghetu A F et al., entitled "Structure of BCOR Corepressor Peptide in Complex with the BCL6 BTB Domain Dimer," Molecular Cell, 29, Feb. 15, 2008, pp. 384-391.

* cited by examiner

*Primary Examiner* — Julie Ha
(74) *Attorney, Agent, or Firm* — Amster, Rothstein & Ebenstein LLP

(57) ABSTRACT

The invention is directed to a compound that binds to a BCL6 lateral groove and prevents binding of a corepressor to the lateral groove. The present invention is further directed to methods for blocking corepressor binding to a BCL6 lateral groove, methods for inhibiting BCL6 repression in a mammalian cell, and methods for treating a mammal with cancer, wherein the cancer requires BCL6 repression. The present invention is further directed to polypeptides comprising a portion of the corepressor binding site for BCL6 and related polynucleotides and vectors.

22 Claims, 18 Drawing Sheets

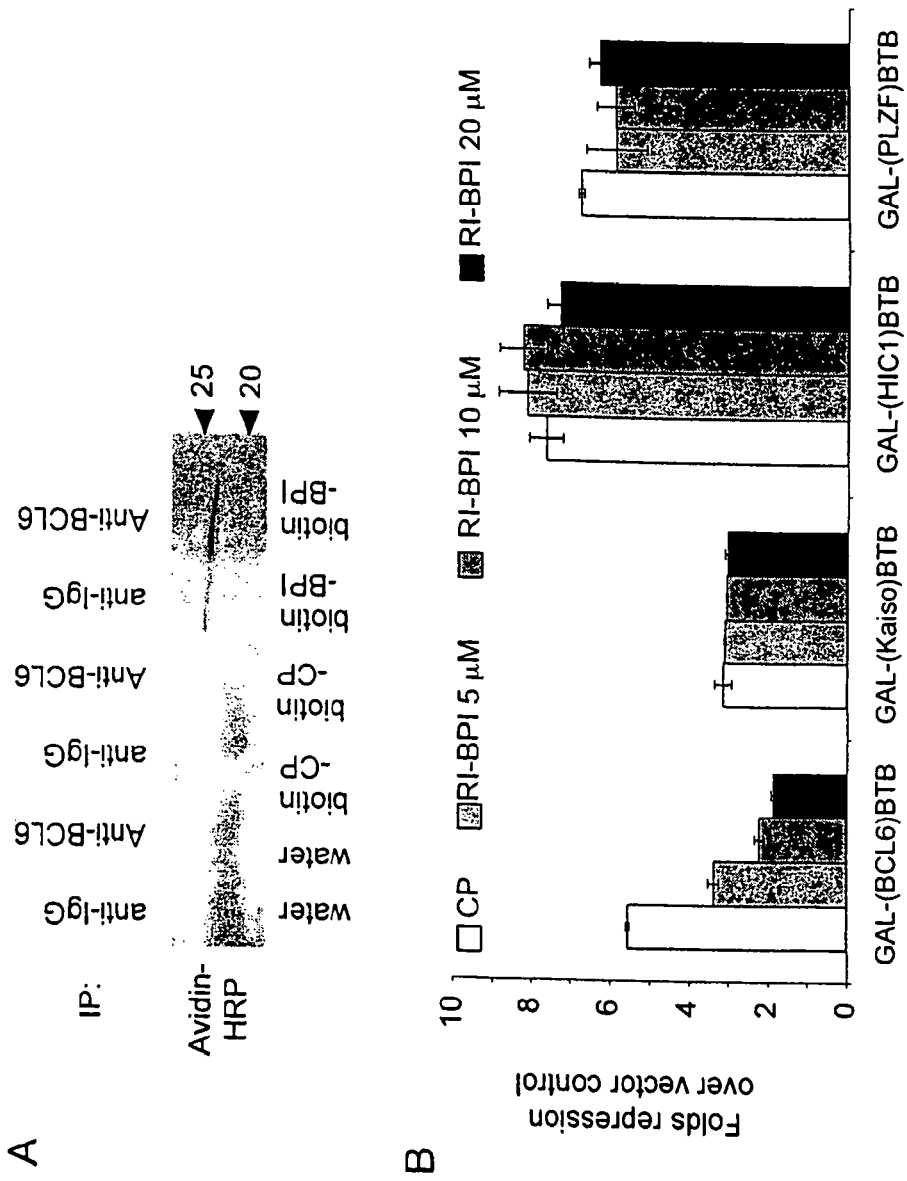
Figure 1 A-B

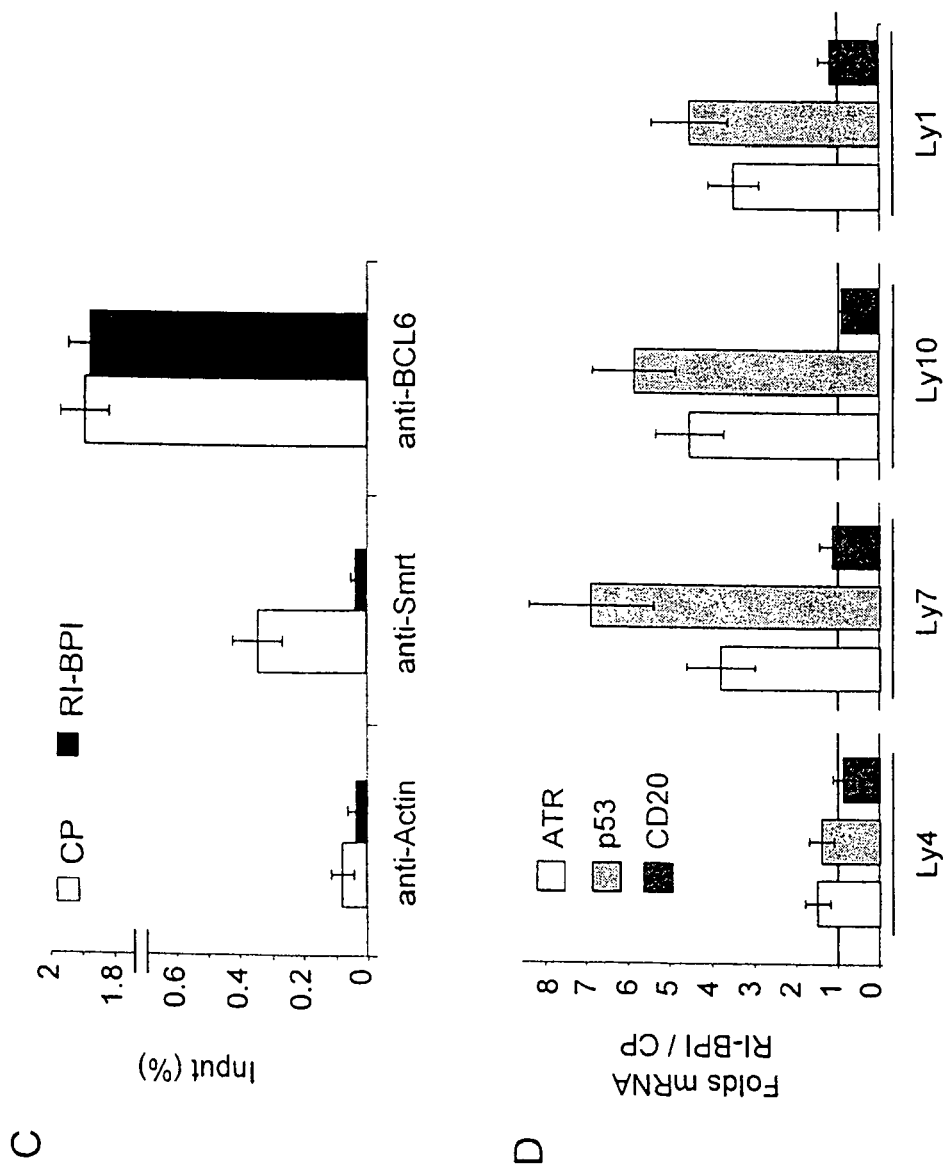
Figure 1 C-D

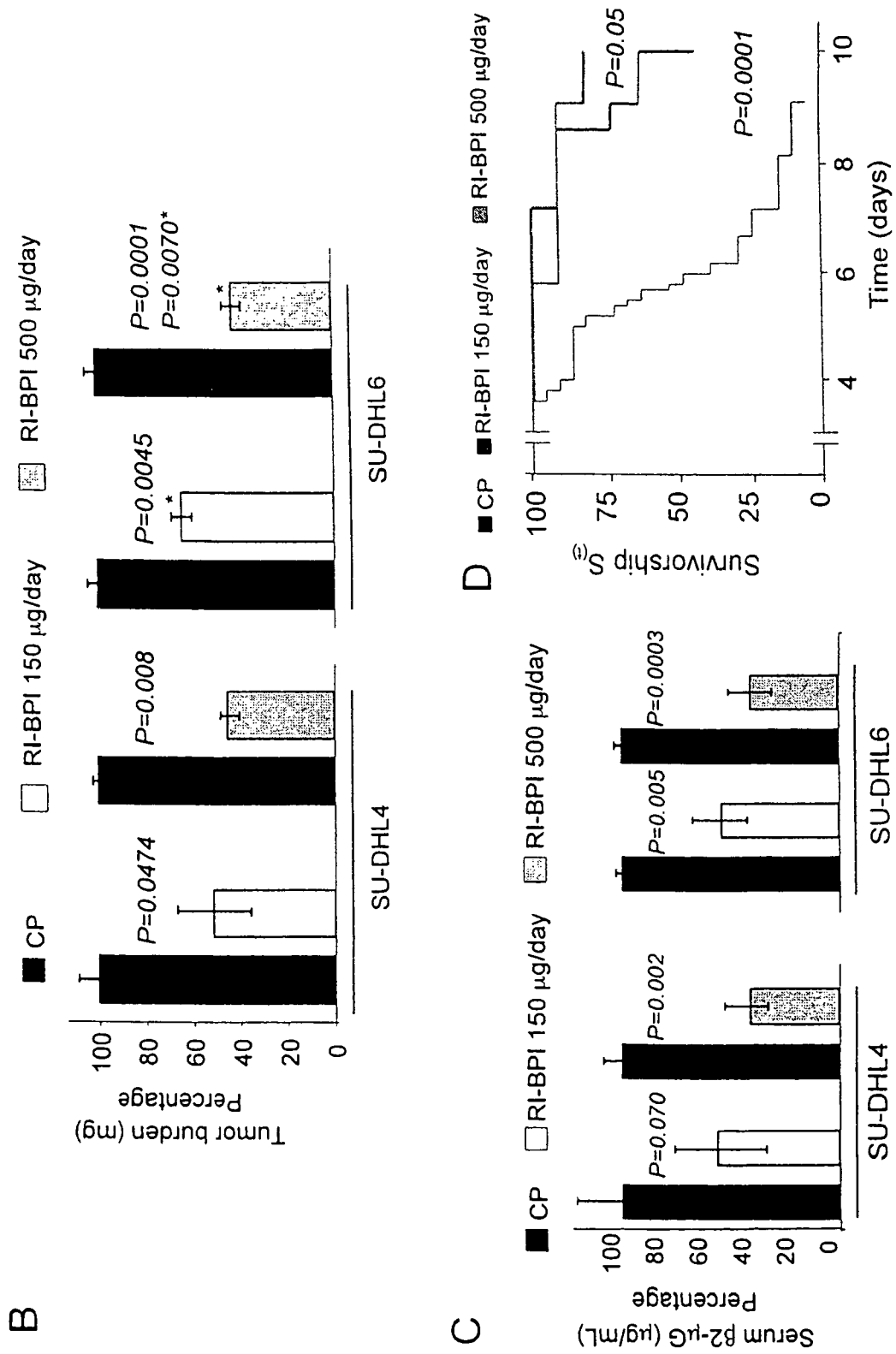
Figure 4 B-D

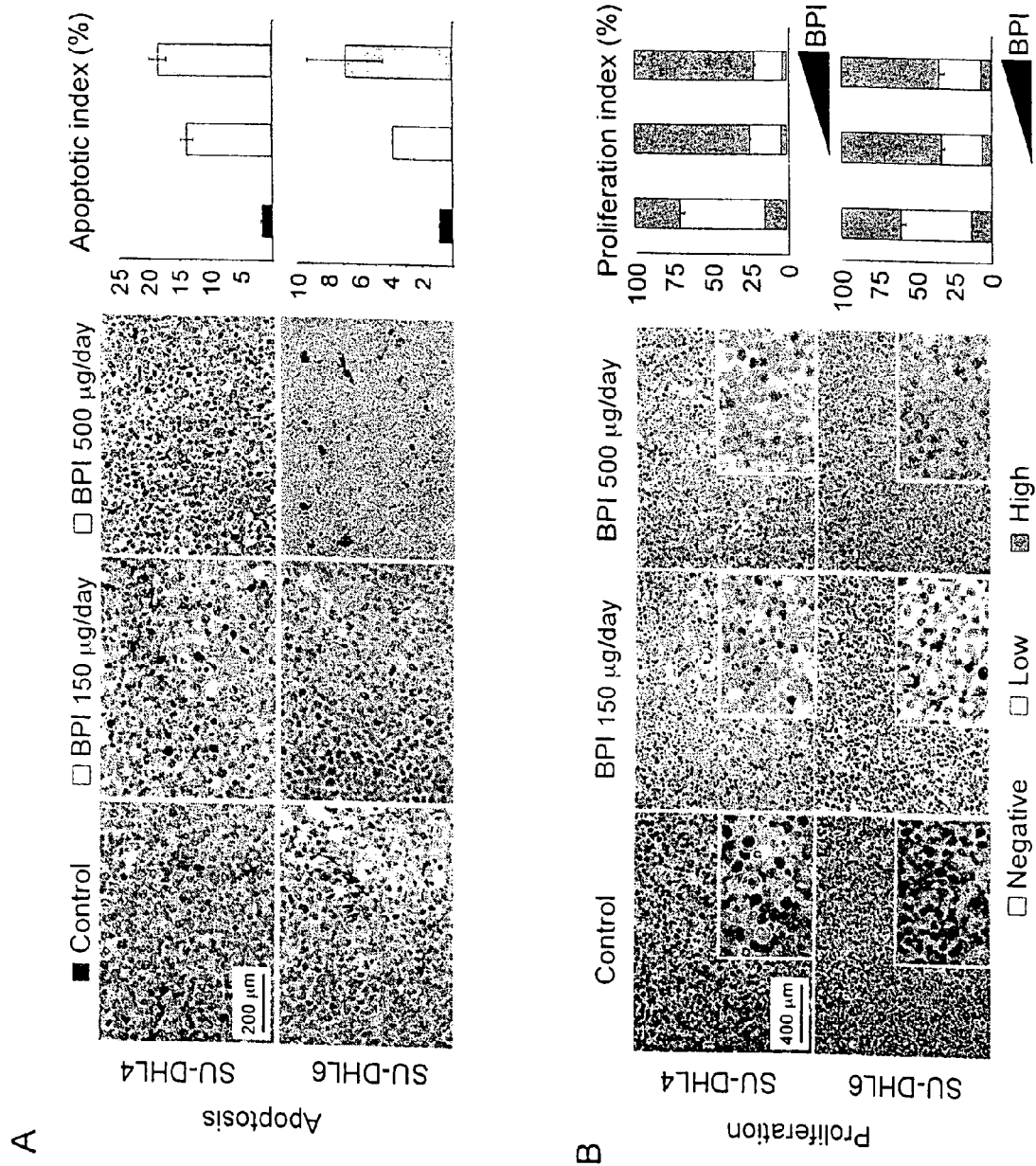
Figure 5 A-B

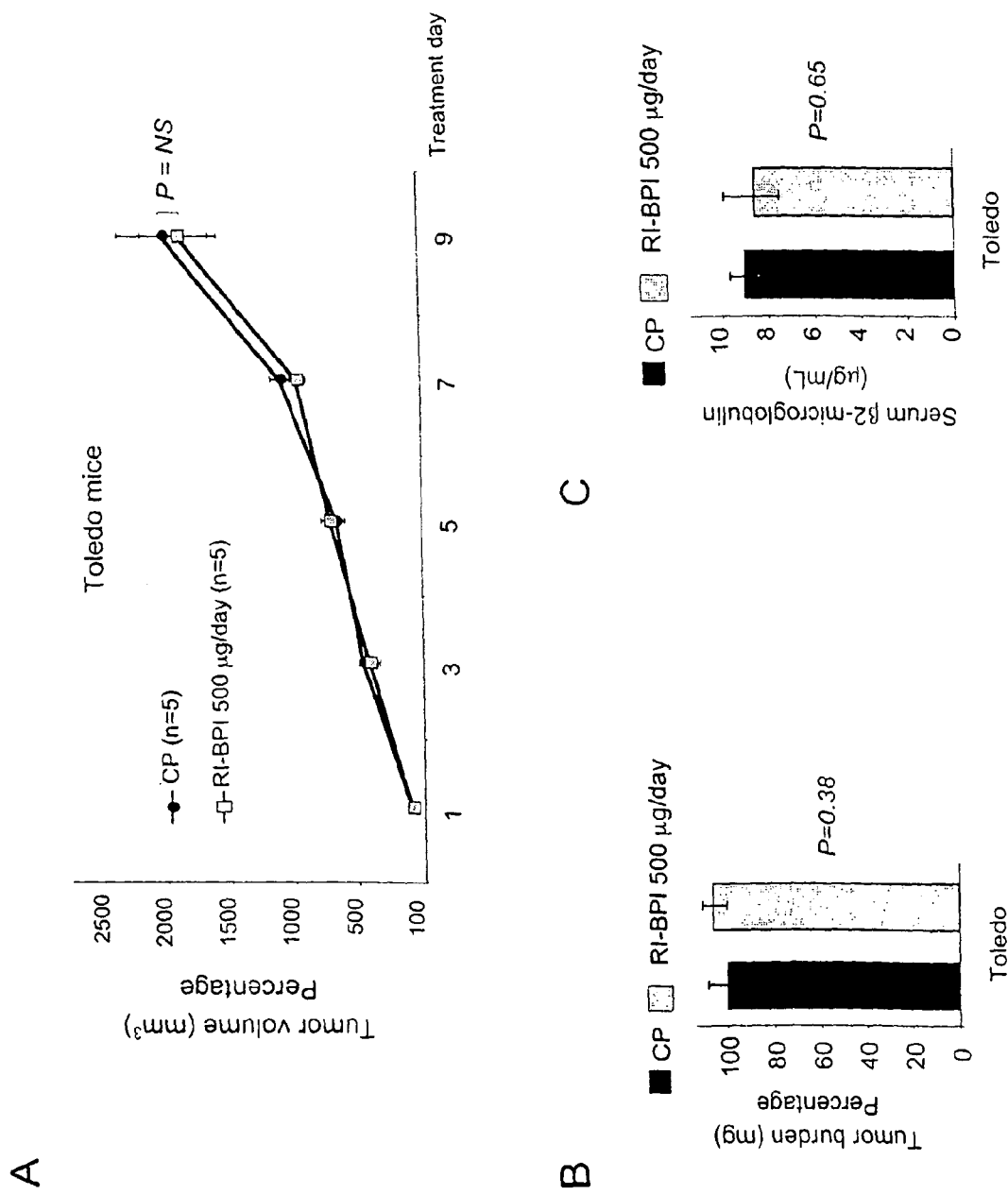
Figure 6 A-C

| Denomination | GI$_{50}$ (mean ± 95%CI) | Dose frequency |
|---|---|---|
| R | >80 μM | 12 |
| S1 | >100 μM | NA |
| S2 | >100 μM | 12 |
| S3 L-BPI | >100 μM | 12 |
| S4 | 95 ± 10 μM | 8 |
| S5 | > 100 μM | NA |
| S6.1 | 61 ± 5.8 μM | 1 |
| S6.2 RI-BPI | 56 ± 7 μM | 1 |
| S6.3 | 68 ± 8.2 μM | 1 |
| S7 | >100 μM | 1 |

Figure 12

METHODS AND COMPOSITIONS FOR INHIBITION OF BCL6 REPRESSION

CROSS-REFERENCE TO RELATED APPLICATIONS

This application is a U.S. national stage entry under 35 U.S.C. §371 of PCT International Patent Application No. PCT/US2009/003483, filed Jun. 10, 2009, and claims priority to U.S. Provisional Patent Application No. 61/132,948, filed Jun. 24, 2008, the contents of which are incorporated herein by reference in their entirety.

STATEMENT OF GOVERNMENT SUPPORT

This invention was made with government support under Grant No. CA104348 awarded by the National Institutes of Health. The government has certain rights in the invention.

FIELD OF THE INVENTION

The present invention generally relates to inhibition of corepressor binding to BCL6. More specifically, the invention is directed to compositions and methods for inhibiting corepressor binding to the BCL6 lateral groove.

BACKGROUND OF THE INVENTION

Throughout this application various publications are referred to by Arabic numerals in brackets. Full citations for these references may be found at the end of the specification immediately preceding the claims. The disclosures of these publications are hereby incorporated by reference in their entireties into the subject application to more fully describe the art to which the subject application pertains.

Expression of the BCL6 (B-Cell Lymphoma 6) transcriptional repressor is required for B-cells to form germinal centers (GC) and undergo immunoglobulin affinity maturation [1,2]. BCL6 contributes to the GC B-cell phenotype of clonal expansion and genetic recombination by repressing target genes involved in DNA damage responses such as ATR (ataxia telangiectasia related), TP53 (tumor suppressor protein p53) and CDKN1A (cyclin dependent kinase inhibitor 1A) [3,4,5]. BCL6 can also repress the PRDM1 (PR domain containing 1, with ZNF domain) gene and thus inhibit plasma cell differentiation of GC B-cells[6,7]. Translocations or mutations of negative regulatory elements that occur as byproducts of class switch recombination or somatic hypermutation can lead to constitutive expression of BCL6[8,9]. Such events are among the most common genetic lesions found in human diffuse large B-cell lymphomas (DLBCL). Animals engineered to recapitulate deregulated expression of BCL6 in germinal center B-cells develop DLBCL similar to the human disease[10,11].

BCL6 is a member of the BTB-POZ (bric a brac, tramtrack, broad complex-pox virus zinc finger) family of proteins. Homo-dimerization of the BCL6 BTB domain forms an extended lateral groove motif along the dimer interface, which is required to recruit the SMRT (Silencing mediator of retinoic acid and thyroid hormone receptor) and N-CoR (Nuclear hormone receptor corepressor) co-repressors[12]. Amino acid side chains protruding into this groove make extensive contact with an 18-residue BCL6 binding domain (BBD) peptide that is conserved between N-CoR and SMRT [12]. The BCL6 lateral groove residues that contact N-CoR and SMRT are unique to BCL6 and are not present in other BTB proteins[12]. A recombinant peptide containing the SMRT BBD along with a cell penetrating TAT domain and other motifs was able to block interaction of BCL6 with SMRT and N-CoR. This BCL6 peptide inhibitor (BPI) could re-activate BCL6 target genes and kill BCL6-expressing DLBCL cell lines in vitro[13]. DLBCL cells thus require the continued presence and function of BCL6 for their survival, suggesting that BCL6 is a bona fide therapeutic target in this disease. Although BPI could kill DLBCL cells at low micromolar concentrations, it was highly unstable and required frequent re-administration to cell cultures in order to detect its biological activities [13]. Therefore, despite the initial effectiveness of BPI, there is a still a great need for a more potent and stable inhibitor.

Due to the importance of BCL6 in B-cell differentiation and DLBCL development, there is a need for a stable, non-immunogenic and non-toxic inhibitor specific for BCL6 capable of disrupting BCL6 repression complexes in DLBCL cells. The present invention addresses that need.

SUMMARY OF THE INVENTION

The present invention is based on the identification of the BCL6 site of corepressor binding, and the discovery that a peptide having the sequence of a portion of the corepressor binding site inhibits corepressor binding to BCL6. This inhibition causes apoptosis of B-cell lymphoma cells expressing BCL6.

Thus, in some embodiments, the invention is directed to a compound that binds to a BCL6 lateral groove and prevents binding of a corepressor to the lateral groove.

The present invention is further directed to methods for blocking corepressor binding to a BCL6 lateral groove.

The present invention is further directed to methods of inhibiting BCL6 repression in a mammalian cell.

The present invention is further directed to methods for treating a mammal with cancer, wherein the cancer requires BCL6 repression.

Finally, the present invention is further directed to a polypeptide comprising a portion of the BCL6 site of corepressor binding, and related polynucleotides and vectors.

BRIEF DESCRIPTION OF THE FIGURES

FIGS. 1A-1D. RI-BPI specifically inhibits the transcriptional and biological function of BCL6. A: BCL6 immunoprecipitation (IP) in Ly1 cell lysates after exposure to RI-BPI$^{biotin}$ or CP$^{biotin}$ (control) peptides. Anti-IgG was used as control for the IP. Detection of complexes was done using avidin-HRP conjugates. B: Reporter assays performed in 293T cells transfected with BTB-fusion constructs as indicated. Cells were exposed to control peptide (white bars) or RI-BPI 5 µM (light grey), 10 µM (dark grey) or 20 µM (black). Fold repression is expressed vs. the effect of each dose on a GAL4-DBD vector control for each experiment, relative to a TK-renilla internal control. C: Chromatin immunoprecipitation from Ly1 cells treated with CP 20 µM (white bars) or RI-BPI 20 µM (black bars) using antibodies against SMRT, BCL6 and actin (as a negative control) and amplifying the promoter region surrounding the BCL6 binding site on the TP53 gene by quantitative PCR. Results are expressed as percentage relative to the input. D: Real-time detection of mRNA of the endogenous BCL6 target genes ATR (white bars) and TP53 (grey bars), and the control gene CD20 (black bars), performed in the BCL6-dependent cell lines Ly7, Ly10 and Ly1 and in the BCL6-independent cell line Ly4, after treatment with RI-BPI 20 μM and CP 20 μM. Results are expressed as fold change in mRNA abundance mediated by RI-BPI over CP.

FIG. 12. The table shows the extrapolated Growth Inhibitory concentration 50% ($GI_{50}$) for the successive versions of BPI in the Ly4 cells used as control for not specific activity. The peptides structure and dose frequency (i.e. the number of doses given over a 48 hour period) are shown in Table 1.

DETAILED DESCRIPTION OF THE INVENTION

Figure 2:
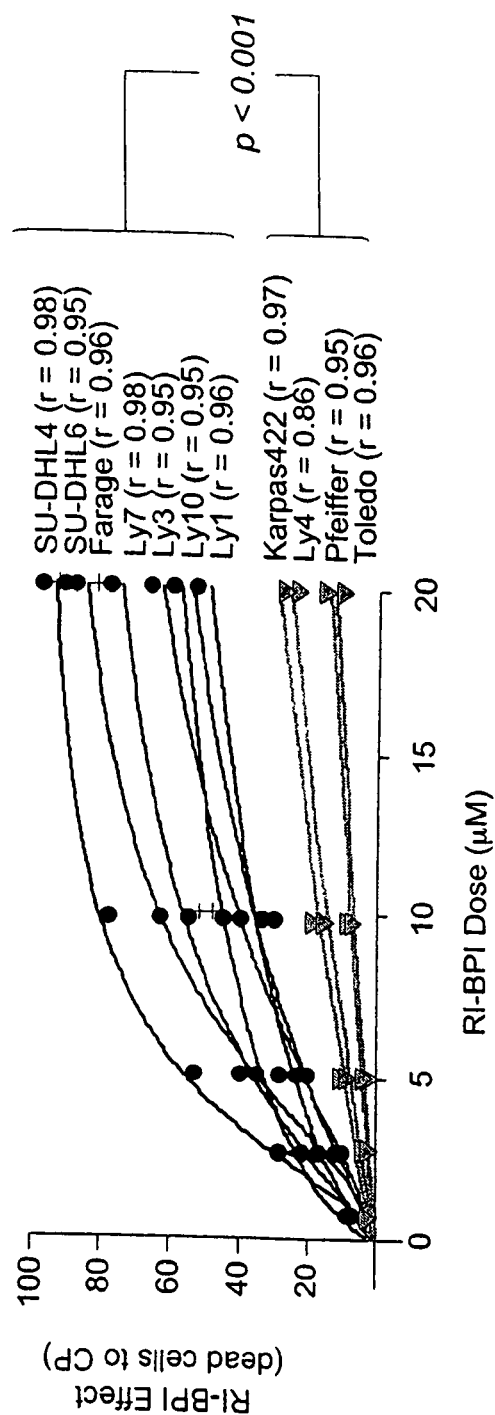
FIG. 2. RI-BPI selectively kills BCR type DLBCL cells. Dose-response curves for RI-BPI in a panel of 11 DLBCL cell lines. The X-axis shows the dose of BPI in μM. The Y-axis shows the effect of RI-BPI as compared to CP on cell viability. BCL6-dependent cell lines (BCR-type) are shown in black circles, while BCL6-independent (OxPhos-type) cell lines are shown in grey triangles. The goodness of fit for the experimental data to the median-effect equation is represented by the linear correlation coefficient (r) obtained from the logarithmic form of this equation. There was a statistically significant difference between the average of the $GI_{50}$s of BCL6-dependent vs. BCL6-independent cell lines (p<0.001, T test).

The present invention is based on the identification of the BCL6 site of corepressor binding, and the discovery that peptides having a portion of the sequence of the corepressor binding site inhibit corepressor binding to BCL6. This inhibition causes apoptosis of B-cell lymphoma cells expressing BCL6.

Thus, in some embodiments, the invention is directed to compounds that bind to the BCL6 lateral groove and prevent corepressor binding. In preferred embodiments, the compound is a peptide or mimetic. These peptides or mimetics preferably comprise the sequence GRGIEHISR (SEQ ID NO:1). In other embodiments, the peptides or mimetics consist of the amino acid sequence GRGIEHISR (SEQ ID NO:1) or the amino acid sequence GRGIEHISRG (SEQ ID NO:2).

As used herein, "mimetics", also known as peptidomimetics, includes any of the many known compounds that behave like peptides, but are made of L-amino acid analogs that are more resistant to degradation than peptides. Examples include peptide analogs, pseudopeptides, depsipeptides, or, preferably, retro-inverso peptides or mimetics of D-amino acids. Any of these peptidomimetics to any particular peptide can be synthesized by the skilled artisan without undue experimentation.

The peptide or mimetic can also comprise one or more functional groups, such as a moiety that facilitates purification, e.g., a $(His)_6$ moiety or an antibody-binding epitope. Another functional group that can be utilized as part of the peptide or mimetic is a moiety that facilitates entry of the peptide or mimetic into a cell, such as the protein transduction domain from the HIV pTAT protein. An additional useful functional group here is a moiety that facilitates detection of the peptide or mimetic, such as a fluorescent moiety, a radioactive moiety, or an antigen. In a preferred embodiment, the compound comprises a TAT sequence and a fusogenic sequence. For example, the peptide or mimetic may be linked directly to the TAT sequence, and the TAT sequence is directly linked to the fusogenic sequence. In another embodiment, the TAT sequence is directly linked to the peptide or mimetic, and the peptide or mimetic is directly linked to the fusogenic sequence. In yet another embodiment, the TAT sequence is directly linked to the fusogenic sequence, and the fusogenic sequence is directly linked to the peptide or mimetic.

For therapeutic uses, the peptide or mimetic is preferably in a pharmaceutically acceptable excipient. Such compositions can be formulated without undue experimentation for administration to a mammal, including humans, as appropriate for the particular application. Additionally, proper dosages of the compositions can be determined without undue experimentation using standard dose-response protocols.

Accordingly, the peptide or mimetic compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The peptide or mimetic compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical peptide or mimetic compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the peptide or mimetic composition may also take place using a nasal tampon or nasal sponge.

In additional embodiments, the invention is directed to methods of blocking corepressor binding to a BCL6 lateral groove. The methods comprise contacting the BCL6 with any of the compounds described above.

In preferred embodiments of these methods, the BCL6 is in a mammalian cell, preferably a cancer cell that requires BCL6 repression. Addition of the peptides to such cells cause apoptosis in a significant percentage of the cells.

It is preferred that cancer cells treated in these methods are in a living mammal. The invention methods would be expected to work in any mammal, however, in the most preferred embodiments, the mammal is a human. Additionally, it is preferred that the cancer cell in these embodiments is a lymphoma cell or breast cancer cell, since those forms of cancer often require BCL6 repression to avoid apoptosis.

It is preferred in these methods that the compound comprises a peptide or mimetic that comprises the sequence of SEQ ID NO:1.

In other embodiments, the invention is directed to methods of inhibiting BCL6 repression in a mammalian cell. The methods comprise treating the cell with any of the above-described compounds. As with the methods described above, the cell is preferably a cancer cell, most preferably a lymphoma or a breast cancer cell. It is also preferred that the cell is in a mammal, most preferably a human. It is also preferred that the compound comprises a peptide or mimetic comprising the sequence of SEQ ID NO:1.

In related embodiments, the invention is directed to methods of treating a mammal with cancer. The methods comprise administering any of the above described compounds, in a pharmaceutically acceptable excipient, to the mammal. In these methods, the cancer requires BCL6 repression. As such, treatment with the peptide prevents corepressor binding and causes apoptosis of the cell.

In preferred embodiments, the mammal is a human; it is also preferred that the cancer is a lymphoma or a breast cancer. As with the methods described above, the preferred compound comprises a peptide or mimetic comprising the sequence of SEQ ID NO:1.

The inventors have also identified a novel polypeptide comprising SEQ ID NO:1. Thus, the invention is further directed to polypeptides comprising SEQ ID NO:1. Also useful are polynucleotides encoding this polypeptide, and vectors comprising this polynucleotide.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods

Cell Lines, Peptides and Drugs.

The DLBCL cell lines OCI-Ly1, OCI-Ly4, OCI-Ly7 and OCI-Ly10 (here in Ly1, Ly4, Ly7 and Ly10) were grown in medium containing 90% Iscove's and 10% FCS, and supplemented with penicillin G/streptomycin, and the DLBCL cell lines Pfeiffer, Toledo, Farage, OCI-Ly3 (here in Ly3), SU-DHL6 and SU-DHL4 were grown in medium containing 90% RPMI and 10% FCS supplemented with penicillin G/streptomycin, L-glutamine and HEPES. Cells were maintained in these conditions during the experiments and peptides were added from a 1000× concentrated stock solution to the 10% serum-containing culture medium. The synthetic peptides (and their biotinylated form) were obtained from Biosynthesis, Inc (Lewisville, Tex.) and stored lyophilized at −20 C until reconstituted with sterile pure acidic water immediately before use (for both in vitro and in vivo experiments). The purity determined by HPLC-MS was 98% or higher for each peptide. The recombinant peptides were obtained and stored as described. The control peptide for R was previously published[13], for S1 and S2 was $NH_2$-YGRKKRRQRRRG-OH (SEQ ID NO:3), for S3 was $NH_2$-GLFGAIAGFIENGWEG-MIDGGRKKRRQRRRG-OH (SEQ ID NO:4), for S4, S5 and S6 was (D aminoacid isomers are shown between parentheses) $NH_2$-G(RRRQRRKKR)GG(DIM)G(EW)G(NEIF)G(AIA)G(FL)G-OH (SEQ ID NO:5); and for S7 was $NH_2$-G(RRRQRRKKR)GG-OH (SEQ ID NO:6). The aminoacid sequence for the TAT peptide was $NH_2$-YGRKKRRQRRRG-OH (SEQ ID NO:7) and for the Fusogenic peptide (Fu) was $NH_2$-GLFGAIAGFIENGWEGMIDG-OH (SEQ ID NO:8).

Reporter Assays.

Dual luciferase assays (Promega, Madison, Wis.) were performed in 293T cells transfected with 100 ng of either $(GAL4)_5$-TK-LUC, $(BCL6)_4$-TK-LUC, (Kaiso)-TK-LUC, (HIC)-TK-LUC, (PLZF)-TK-LUC, and the corresponding expression vectors plus a renilla reporter as internal control, as published [13]. Cells were treated with 20 µM of RI-BPI or CP for 12 hours and the luminescence was measured in a Polarstar Optima microplate reader (BMG Labtechnologies, Germany).

In Vitro BPI Binding.

To determine the in vitro RI-BPI binding to BCL6, $10^7$ Ly1 cells were lysed in modified RIPA buffer (50 mM Tris, 250 mM NaCl, 1% Nonidet P-40, 0.5% deoxycholate, 0.1% SDS) containing a protease inhibitor cocktail. Cell lysates were exposed to RI-BPI$^{biotin}$ or CP$^{biotin}$ for 1 hour and incubated with anti-BCL6 (N3, Santa Cruz, Santa Cruz, Calif.) or anti-IgG (Santa Cruz) as control. The immunocomplex was pulled-down using protein-A agarose beads and eluted with loading buffer (SDS 1%, NaCO3H 100 mM). The proteins were transferred to a PVDF membrane (Bio-Rad, Hercules, Calif.) and incubated with a solution of avidin-biotinylated-peroxidase (Vectastain ABC, Vector Laboratories, Burlingame, Calif.). The complex was visualized using luminol (Santa Cruz) as chemiluminescent substrate for peroxidase.

Chromatin Immunoprecipitation (ChIP) Analysis.

ChIP was made as previously described with modifications [16] briefly $10^8$ Ly1 cells were treated for 4 hours with 20 µM of RI-BPI or CP, and then fixed with 1% formaldehyde. Cell lysates were sonicated using a Bioruptor (Diagenode Inc., New York, N.Y.). BCL6 N-3 (Santa Cruz), SMRT (Upstate, Lake Placid, N.Y.) and actin (Santa Cruz) antibodies were added to the pre-cleared sample and incubated overnight at 4 C. Then, protein-A beads were added, and the sample was eluted from the beads followed by de-crosslinking. The DNA was purified using PCR purification columns (Qiagen, Valencia, Calif.). Quantification of the ChIP products was performed by quantitative PCR (DNA Engine Opticon 2, Bio-Rad) using SyBr Green (Applied Biosystems, Foster City, Calif.). Primers were designed to verify binding of BCL6 and SMRT at possible BCL6/SMRT binding sites in the p53 locus based on the report of Phan et. al. [4].

Real Time PCR.

Harvested tumors from xenotransplanted mice were kept in RNAlater (Qiagen) at −80 C to stabilize RNA. We extracted RNA from $10^4$ peptide-treated and control cells, and from about 20 mg of peptide-treated and control tumors using RNeasy kit (Qiagen) following the manufacturer instructions. We synthesized cDNA using Superscript First Strand cDNA synthesis kit (Invitrogen, Carlsbad, Calif.). We amplified GAPDH, CD20, and ATR using published primers sequences [3,16] and p53 with the following primers: 5'-AATCAAC-CCACAGCTGCAC-3' (SEQ ID NO:9) and 5'-TCTTCT-GTCCCTTCCCAGAA-3' (SEQ ID NO:10). Thermal cycler conditions were: initial step of 10 min at 95 C followed by 40 cycles of 15 sec at 95 C (denature) and 1 min at 60 C (anneal/extend). For the cell lines, the $C_T$ values of GADPH were subtracted from the correspondent genes of interest ($\Delta C_T$). The standard deviation of the difference was calculated from the standard deviation of the $C_T$ values (triplicates). Then, the $\Delta C_T$ values of the peptide-treated cells were expressed relative to their respective control-treated cells using the $\Delta\Delta C_T$ method. The folds of expression for each gene in cells treated with peptide/drug relative to control treated cells is determined by the expression: $2^{-\Delta\Delta C_T}$. Results were represented as folds of expression with the standard error of the mean (SEM) for 3 series of triplicates. For tumor tissues, we construct a standard curve for $C_T$ values of each gene of interest (p53, ATR and GAPDH) by the cDNA amount (in ng) of an external calibrator (Ly1 cell line). Then, we calculated the amount of each gene of interest in the experimental samples. Results are expressed as normalized values (ng p53/ng GAPDH and ng ATR/ng GAPDH) in arbitrary units.

Growth Inhibition Determination.

DLBCL cell lines were grown at its respective concentration that were sufficient to keep the untreated cells in exponential growth over the 48 h peptide exposure time. Cell viability was determined by using a fluorometric resazurin reduction method (CellTiter-Blue, Promega) following the manufacturer instructions. The fluorescence ($560_{Ex}/590_{Em}$) was determined using the Polarstar Optima microplate reader (BMG Labtechnologies). The number of viable cells in each treated well was calculated by using the linear least-squares regression of the standard curve. Optical density was determined for 6 replicates per treatment condition or standard. Cell viability in peptide-treated cells was normalized to their respective controls. Cell viability was verified by the Sulforhodamine B assay (Sigma, Milwaukee, Wis.) following manufacturer's instructions with minor modifications for suspended cells. Experiments were carried out in triplicates and data are represented as percentage of growth inhibition to respective control with 95% confidence interval. CompuSyn software (Biosoft, Great Shelford, Cambridge, UK) was used to plot the dose-effect curves and to determine the concentration a peptide that inhibits 50% the growth of cell lines compared to control peptide treated cells ($GI_{50}$).

Primary Cells Treatment.

Patient tissues were obtained in accordance with the guidelines and approval of the Institutional Review Board and in accordance with the Declaration of Helsinki. These were leftover, de-identified tissues from routine surgical biopsies. Single cells suspensions from lymph node biopsies were obtained by physical disruption of tissues (using scalpels and cell restrainers), followed by cell density gradient separation (Fico/Lite LymphoH, Atlanta Biologicals, Lawrenceville, Ga.). Cell number and viability were determined by trypan blue dye exclusion and cells were cultivated in medium containing 80% RPMI and 20% FCS supplemented with penicillin G/streptomycin, L-glutamine and HEPES for 48 h. Three different cell concentrations in triplicates were exposed to three doses of control and active peptides (1, 5 and 10 µM). After 48 h of exposure, viability was determined by using a fluorometric resazurin reduction method (CellTiter-Blue, Promega) and trypan blue dye exclusion as above. The BCL6 protein status was determined in paraffin-embedded samples by IHC using anti-BCL6 (Dako, Carpinteria, Calif.) as described.

Mice Xenotransplant Models.

All procedures involving animals followed NIH protocols and were approved by and done accordingly to guidelines of the Animal Institute Committee of the Albert Einstein College of Medicine. Six to eight-week old male severe combined immunodeficiency (SCID) mice were purchased from the National Cancer Institute (NCI, Bethesda, Md.) and housed in a barrier environment. Mice were subcutaneously injected in the left flank with low-passage $10^7$ human DLBCL cells (SU-DHL6, SU-DHL4 and Toledo). Tumor volume was monitored every other day using electronic digital calipers (Fisher Scientific) in two dimensions. Tumor volume was calculated using the formula: Tumor Volume ($mm^3$)=(smallest $diameter^2$×largest diameter)/2. When tumors reached a palpable size (approximately 75 to 100 $mm^3$ after 19 to 36 days post-injection depending on the cell line), the mice were randomized assigned to different treatment arms; in consequence these experiments were all performed once tumors had fully formed in the animals. Peptides were stored lyophilized at −20 C until reconstituted with sterile pure acidic water immediately before used and were administered by intra-peritoneal injection. Mice were weighted every other day. All mice were euthanized by cervical dislocation under anesthesia when at least 2/10 tumors reached 20 mm in any dimension (equivalent to 1 gram tumors) that for the cell lines used corresponded to day 10 (or 9 days of treatment). At the moment of euthanasia, blood was collected (StatSampler, Iris, Westwood, Mass.) and tumors and other tissues were harvested and weighted.

Mice Toxicity Studies.

Six to eight-week old male C57BL mice were purchased from the NCI and housed in a barrier environment. Peptides were stored, reconstituted and administered as before. RI-BPI and control were administered at 500 pig daily for the first 3 weeks and weekly for the following 49 weeks. Mice were weighed every other day during the 3-week period and weekly thereafter. All mice were euthanized by cervical dislocation under anesthesia accordingly to predetermined time points (3-weeks and 1 year). At the moment of euthanasia, blood was collected and the organs were harvested and weighted. All organs and tissues underwent careful macroscopic and microscopic (hematoxilin-eosin staining) examination.

Mice Germinal Center Models.

Fifteen 8-week-old male C57BL mice were intraperitoneally injected with 0.5 ml 2% v/v sheep red blood cells (Cocalico Biologicals Inc). The day after the immunization, mice were randomized in 3 groups (n=5) and after 3 days were daily treated with vehicle, CP or RI-BPI 500 µg for 7 days. All mice were euthanized by cervical dislocation under anesthesia at day 10, and the whole spleen were removed, weighed, fixed and embedded in paraffin. B-cells were identified by a biotinylated anti-CD45R (Caltag, Invitrogen) and germinal center activated B-cells by a biotinylated peanut agglutinin (Vector). Color was developed with diaminobenzoate chromogen peroxidase substrate (Vector). Pictures were taken using a color camera (AxioCam, Zeiss, Germany) attached to an AxioSkop II light microscope (Zeiss) and processed using ImageJ (NHI). PNA and CD45R clusters were counted and measured in each whole-spleen digitally reconstituted longitudinal sections.

Human β2-microglobulin.

Serum levels of human β2-microglobulin were determined in the mice at day 10 by enzyme immunoassay (Quatikine IVD, R&D Systems, Minneapolis, Minn.) following the manufacturer instructions. The mean absorbance ($A_{450}$-$A_{620}$) values for each set of triplicates and standards were measured using the Polarstar Optima microplate reader (BMG Labtechnologies) and concentrations were calculated using a four-parameter logistic curve fit (SigmaPlot, Systat Software, San Jose, Calif.).

Apoptotic Index.

The DNA fragmentation coupled to the apoptotic response was detected in morphologically identifiable nuclei and apoptotic bodies present in formalin-fixed paraffin-embedded tumors by the TUNEL assay (ApopTag, Chemicon, Temecula, Calif.) following the manufacturer instructions with optimization. Tissue slides were pre-treated with 0.5% trypsin for 15 minutes (Zymed, San Francisco, Calif.), to improve the exposure of DNA.

Proliferation Index.

PCNA was identified by immunohistochemistry as previously described [17]. Briefly, deparaffinized slides were antigen retrieved in citrate buffer pH 6.0 (Zymed) then 1:1000 anti-PCNA (Santa Cruz) was applied, followed by incubation with a corresponding biotinylated-conjugated secondary antibody (Vector). Slides with a preformed avidin and biotinylated horseradish peroxidase macromolecular complex, Vectastain ABC (Vector) were incubated. Color was developed with diaminobenzoate chromogen peroxidase substrate (Vector). PCNA immunohistochemistry results were scored using ImageJ software (National Institutes of Health, Bethesda, Md.).

Mitotic Index.

Mitotic cells were identified by using standard hematoxylin and eosin stain of the tumors in pictures taken using a color camera (AxioCam, Zeiss) attached to an AxioSkop II light microscope (Zeiss) and processed using ImageJ (NHI). The index represents the number of mitotic cells over total number of cells. A minimum of 1000 cells were counted per tumor.

BPI Distribution in Tumors.

The amount of L-BPI$^{biotin}$ and RI-BPI$^{biotin}$ in the serum of mice was determined by using the Quant-Tag Biotin kit (Vector) following the manufacturer instructions. Standards with known concentration of biotin were used to generate a curve to calculate the concentration of biotin in the serum samples. HPLC-MS analysis indicated that 1 mol of biotin was bound to 1 mol of peptide.

Serum Kinetic of BPI.

L-BPI$^{biotin}$ and RI-BPI$^{biotin}$ peptides were detected by histochemistry in tumor tissues using Texas red-avidin (Vector). Briefly, tumor sections were deparaffinized and hydrated trough xylene and graded ethanol series, followed by rinses and incubation with TR-avidin 1 h at RT in buffered saline solution pH 8.2. Slides were mounted with permanent mounting medium (Vectashield Hard set, Vector) to prevent photobleaching and pictures were immediately taken using a color camera (AxioCam, Zeiss) attached to an AxioSkop II fluorescent microscope (Zeiss).

Immunogenicity Studies.

Serum from C57/black mice treated with RI-BPI and controls were stored at −80 C until used. To detect anti-RI-BPI antibodies present in the serum, ELISA arrays in streptavidin-coated plates (Reacti-Bind, Pierce, Rockford, Ill.) were performed. Briefly, these plates were incubated with three different concentrations of RI-BPI$^{biotin}$ or L-BPI$^{biotin}$ diluted in 1% BSA followed by incubation with 10 different triplicates dilutions (1:10 to 1:10,000) of serum and controls. Then, 50 μL of alkaline phosphatase conjugated goat-IgG anti-mouse-IgG (Zymed) in triplicates (in 1% BSA) were added to each well. The plates were developed using p-nitrophenyl phosphate as substrate solution (Sigma) and read at 405 nm using the Polarstar Optima microplate reader (BMG Labtechnologies).

Statistics.

The comparisons between treated and control mice were done using two-tailed T-test (Statistix, Analytical Software, Tallahassee, Fla.). Survival time was considered as the time elapsed (in days) from the start of the treatment ($T_0$) until death or until the tumor volume increase 10 times from $T_0$ (whatever event occurs first). Survival curves were calculated using the Kaplan-Meier method and groups were compared using Gehan-Wilcoxon test for multiple samples and Cox's F test for two-groups comparisons (Statistix). Serum concentrations of human β2-microglobulin in mice were correlated with tumor weight using the Pearson's coefficient (Statistix).

Results

Synthetic Short Forms of BPI Preserve its Anti-Lymphoma Activity.

It was previously reported that a recombinant BCL peptide inhibitor (BPI) containing the SMRT 21-residue BCL6 binding domain (BBD) could specifically inhibit the transcriptional repressor activity of the BCL6 BTB domain [13]. BPI consisted of 120 amino acids and also included a TAT domain for cellular penetration, an HA tag for immunodetection, a $(HIS)_6$ tag for purification purposes, and linker sequences. Although BPI could kill DLBCL cells at low micromolar concentrations, it was highly unstable and required frequent re-administration to cell cultures in order to detect its biological activities [13]. Based on these proof of principle data, it was hypothesized that inhibition of the BCL6 BTB domain might be an effective means for delivering targeted therapy against DLBCL. In order to test whether such an approach was feasible, a rational design strategy was employed to generate superior inhibitors with drug-like properties that could be rigorously tested in vitro and in vivo and potentially translated to the clinic.

DLBCL cell growth inhibition was chosen as the most relevant screening assay to compare and contrast the biological activity of BPI and its derivatives. Recombinant BPI displayed an average $GI_{50}$ of 11.3 μM when given every four hours for a period of 48 hours (i.e. dose frequency (DF)=12) in dose response experiments performed in three DLBCL cell lines known to be biologically dependent on BCL6 (ly1, Ly7 and Ly10) [13,16]. Growth inhibition was measured by a metabolic viability assay and verified by trypan blue exclusion and were performed in biological quintuplicates. The anti-lymphoma activity of BPI is dependent on the balance between cell penetration, stability and binding to BCL6. The goal was to identify peptides that potently and specifically inhibit BCL6 within lymphoma cells and that would be biologically active after a single dose. Table 1 summarizes the data comparing successive generations of new peptides. For all peptides, the $GI_{50}$ is represented as the total amount of peptide administered over the course of the 48 hr treatment period (e.g. for recombinant BPI, the $GI_{50}$ of 11.3 μM is a 48 hr total, so that an average of 900 ng of peptide were administered at each 4 hour interval). As a control for non-specific toxicity, all peptides were also tested against a non-targeted control peptide (CP) and to the Ly4 DLBCL cell line, which were previously showed to be biologically independent of BCL6[13,16].

TABLE 1

| Denomination | Peptide structure | GI$_{50}$ (mean ± 95% CI) | | Dose frequency |
|---|---|---|---|---|
| R | His6—TAT—HA tag—GLVATVKEA—GRSIHEIPR—EEL | 11.3 ± 3 | µM | 12 |
| S1 | TAT—GLVATVKEA—GRSIHEIPR—EEL | >100 | µM | NA |
| S2 | TAT—GRSIHEIPRG | 21.7 ± 3.2 | µM | 12 |
| S3 L-BPI | Fu—TAT—GRSIHEIPRG | 14.2 ± 2 | µM | 12 |
| S4 | Fu—TAT—GRSIHEIPRG | 14.4 ± 2.2 | µM | 8 |
| S5 | GRPIEHISR—TAT—Fu | >100 | µM | NA |
| S6.1 | GRGIEHISR—TAT—Fu | 18 ± 3 | µM | 1 |
| S6.2 RI-BPI | TAT—GRGIEHISR—Fu | 16.5 ± 3.2 | µM | 1 |
| S6.3 | TAT—Fu—GRGIEHISRG | 25.3 ± 3.4 | µM | 1 |
| S7 | TAT—GRGIEHISRG | 96 ± 5 | µM | 1 |

A synthetic peptide (peptide S1 in Table 1) was next generated, containing only the TAT domain along with the 21 aminoacids of the BBD motif. S1 proved to be difficult to synthesize for technical reasons pertaining to amino-acid cleavage and was not active compared to the original BPI molecule. One possible reason for this could be charge interference between the negatively charged EEL tail of BPI and the positively charged TAT domain. To overcome this limitation, shorter peptides that are easier to synthesize and lack the EEL motif were generated. In order to select the most active BBD residues, the structure of the BCL6-SMRT interface was first analyzed. It was noted that a sequence of nine SMRT BBD amino acids (GRSIHEIPR) (SEQ ID NO:11) make the greatest number of contacts to BCL6 and form a loop deep within the interface between BTB monomers [12]. The TAT-GRSIHEIPR (SEQ ID NO:11) peptide displayed an average GI$_{50}$ of 21.7 µM when administered at a dose frequency of 12 (i.e. 1.8 µM per dose), suggesting that shorter BPI forms could retain the activity of the longer peptide and might be viable substrates for further derivation (peptide S2 in Table 1).

Inclusion of a Fusogenic Motif Enhances the Activity of BPI.

Figure 8:
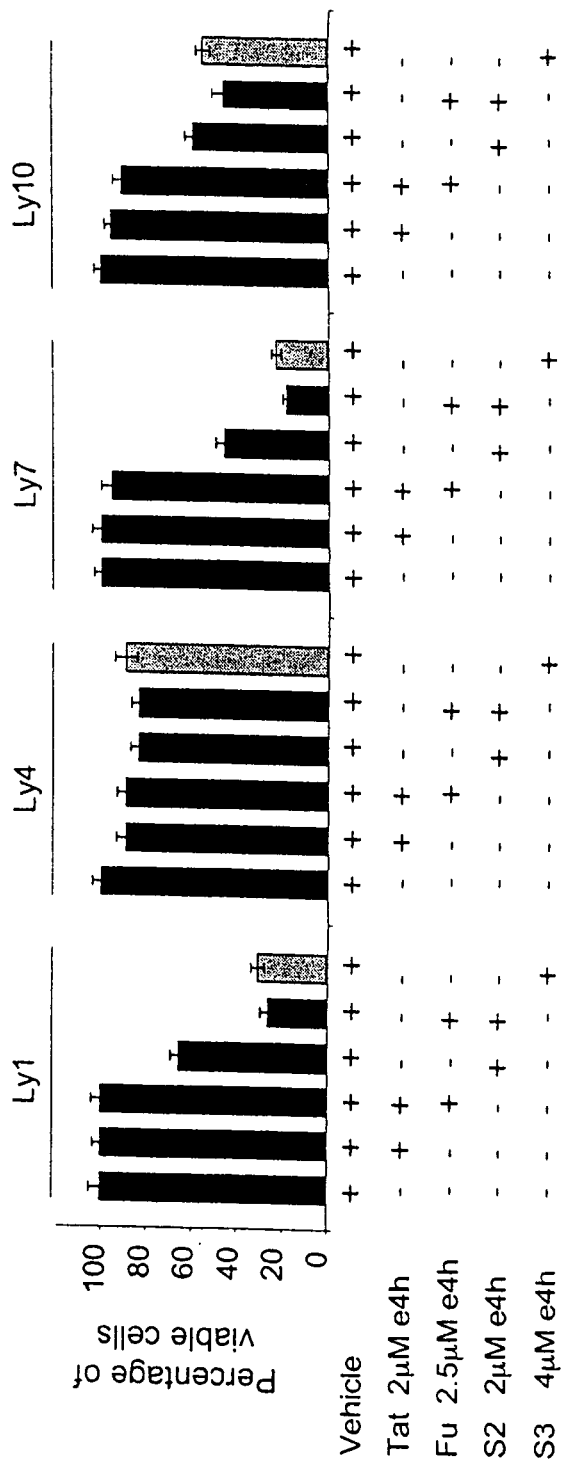
FIG. 8. Fusogenic motif enhances the biological activity of BPI. A: Effect of different peptide design (X-axis) on DLBCL viability (Y-axis). The fusogenic peptide (Fu) alone or in combination with a TAT peptide had little or no effect on cells. Co-administration of the S2-BPI with Fu significantly enhances its anti-lymphoma activity in BCL6 dependent DLBCL cells (Ly1, Ly7 and Ly10) but not in the BCL6 independent Ly4 cell line. A mass-equivalent dose of the combined Fu-TAT-GRSIHEIPR (S3) (SEQ ID NO:11) peptide was similar in efficacy to the concomitant administration of S2 plus Fu. All the peptides were administered every 4 h during a 48 h interval.

Wadia et. al. showed that combination with a TAT-fusogenic peptide could enhance release of cell penetrating peptides from within macropinosomes [14]. Accordingly, it was found that co-administration of the S2-BPI with a TAT-fusogenic peptide (Fu) could significantly enhance its anti-lymphoma activity in BCL6 dependent DLBCL cells but not in the BCL6 independent Ly4 cell line (FIG. 8). The fusogenic peptide alone or in combination with a TAT peptide had little or no effect on cells. Since administering two peptides is less efficient and more costly than giving a single peptide, it was considered whether including the fusogenic motif within S2 might offer an equivalent benefit. A mass-equivalent dose of the combined Fu-TAT-GRSIHEIPR (S3) (SEQ ID NO:11) peptide was similar in efficacy to the concomitant administration of S2 plus fusogenic peptides, suggesting that the built-in capacity to enhance release of peptides from macropinosomes could improve the efficacy of BPI. The average GI$_{50}$ of S3 was 14.2 µM when administered every 4 hours (1.2 µM per dose).

Retroinverso BPI is a Stable Drug-Like BCL6 Inhibitor.

Synthesis of cell penetrating peptides in the retroinverso configuration was shown to enhance their biological activity since they retain a similar structural configuration but are resistant to cleavage by serum or cellular proteases [18]. It was previously shown that retro-inverso TAT and fusogenic motif are fully functional [18]. In order to determine whether peptide instability was solely due to cleavage of the TAT, fusogenic motif or the BBD, a hybrid form of BPI (S4) was generated containing retro-inverso TAT and Fu with the normal L-amino acid GRSIHEIPR motif (SEQ ID NO:11) (Table 1). The S4-BPI displayed a GI$_{50}$ of 14.4 µM, identical to the all L version even when administered at longer intervals (every 6 hs, DF=8). The data suggest that although modifying TAT and Fu improves the stability of the peptide, loss of BBD function was still a limiting factor. However, when the entire peptide was built in retro-inverso configuration (S5), it no longer displayed specific activity (Table 1).

BPI is an unstructured peptide that adopts a pseudo structure when bound to BCL6[12]. One possible explanation for loss of activity was the presence of a proline residue within the GRSIHEIPR motif (SEQ ID NO:11), since proline adopts a stereospecific conformation that would alter the shape of the peptide in the retroinverso configuration. Therefore, whether switching from a proline to a glycine would restore the function of the BBD motif was tested, presumably by allowing it sufficient flexibility to adopt its bound conformation. Three versions of the full retro-inverso peptide with P to G mutations were generated, each containing the BBD in a different order in relation to TAT and Fu sequences. All three of these peptides (S6.1, S6.2 and S6.3—Table 1) displayed powerful anti-lymphoma activity against BCL6 dependent but not BCL6 independent DLBCLs cells, even when administered as a single dose (GI$_{50}$ of 18 µM, 16.5 µM and 25.3 µM, respectively). Therefore, maximal biological activity was achieved by converting the entire BPI molecule into a protease-resistant form.

Finally, it was considered whether the improved stability of retro-inverso BPI might render it unnecessary to include a fusogenic motif and allow for a shorter peptide to be used (Table 1). However, the retroinverso TAT-BBD (S7-BPI) was significantly weaker than then the fusogenic containing S6 peptides.

RI-BPI is a Specific Inhibitor of BCL6 Transcriptional Repressor Function.

Figure 9:
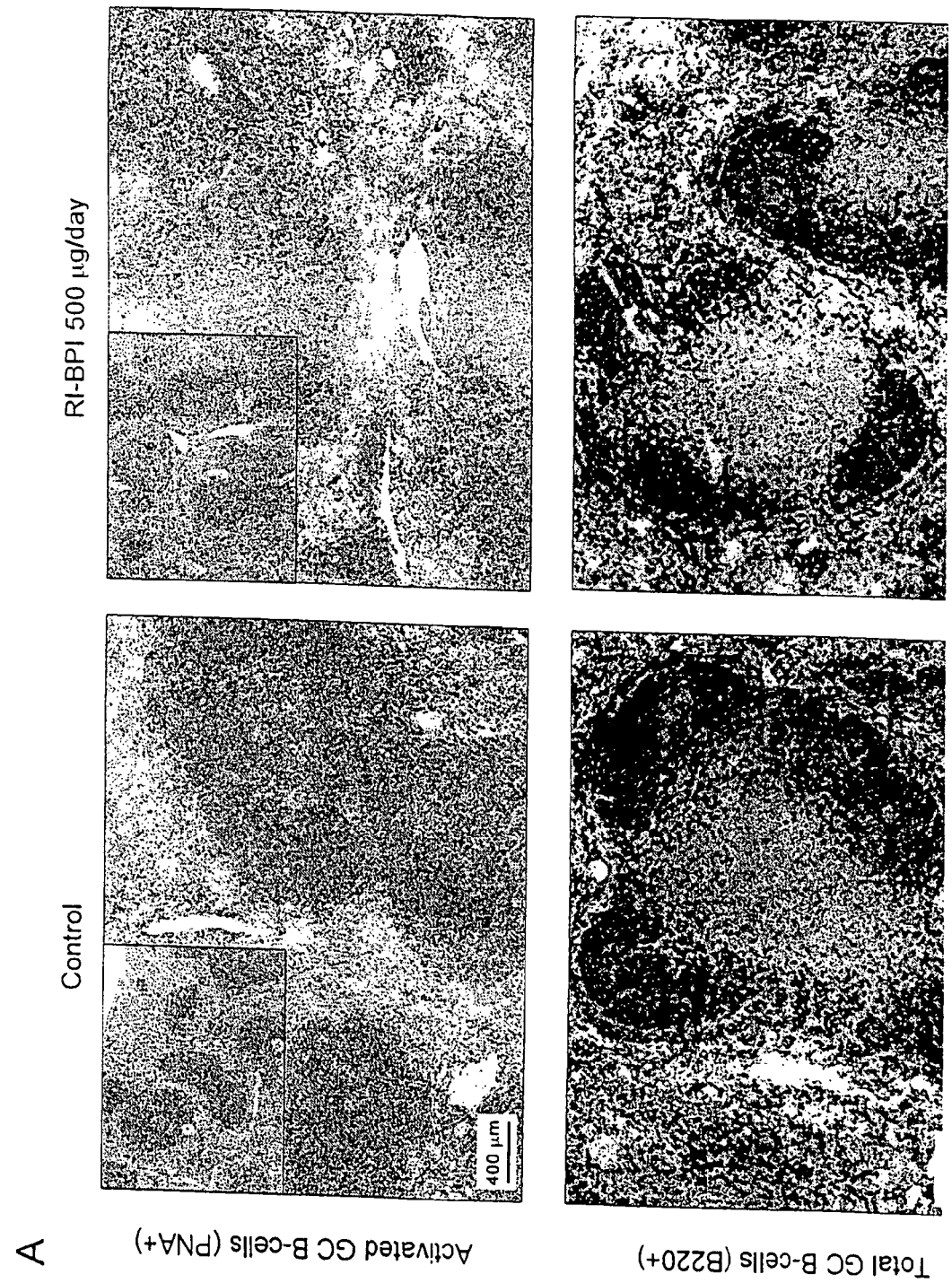
FIGS. 9A-9B. RI-BPI affects the formation of germinal centers in immunized mice. Sheep red blood cells were administered intraperitoneally in 10 C57BL/6 mice to induce a T-cell dependent immune response and generate germinal centers. On day 3, the mice were randomized in 2 groups (n=5 per group) and treated intraperitoneally with 500 of RI-BPI or control peptide per day. After 7 days of injections the animals were sacrificed and spleens were examined for formation of germinal centers by peanut agglutinin (PNA) histochemistry. A: Representative images of spleens from control and treated mice showing PNA+ (activated GC B-cells, upper panel) and B220+ (total GC B-cells, lower panel) clusters in brown. Hematoxilin was used as counterstaining (blue). B: Number (left panel) and size (right panel) of PNA+ clusters from (A). PNA clusters were counted and measured in each whole-spleen digitally reconstituted longitudinal sections, and data represent the median of 5 mice with SD. Images were processed using Image J software. P values were obtained with T-test. LPF: Low power field (40× final magnification).
Figure 9:
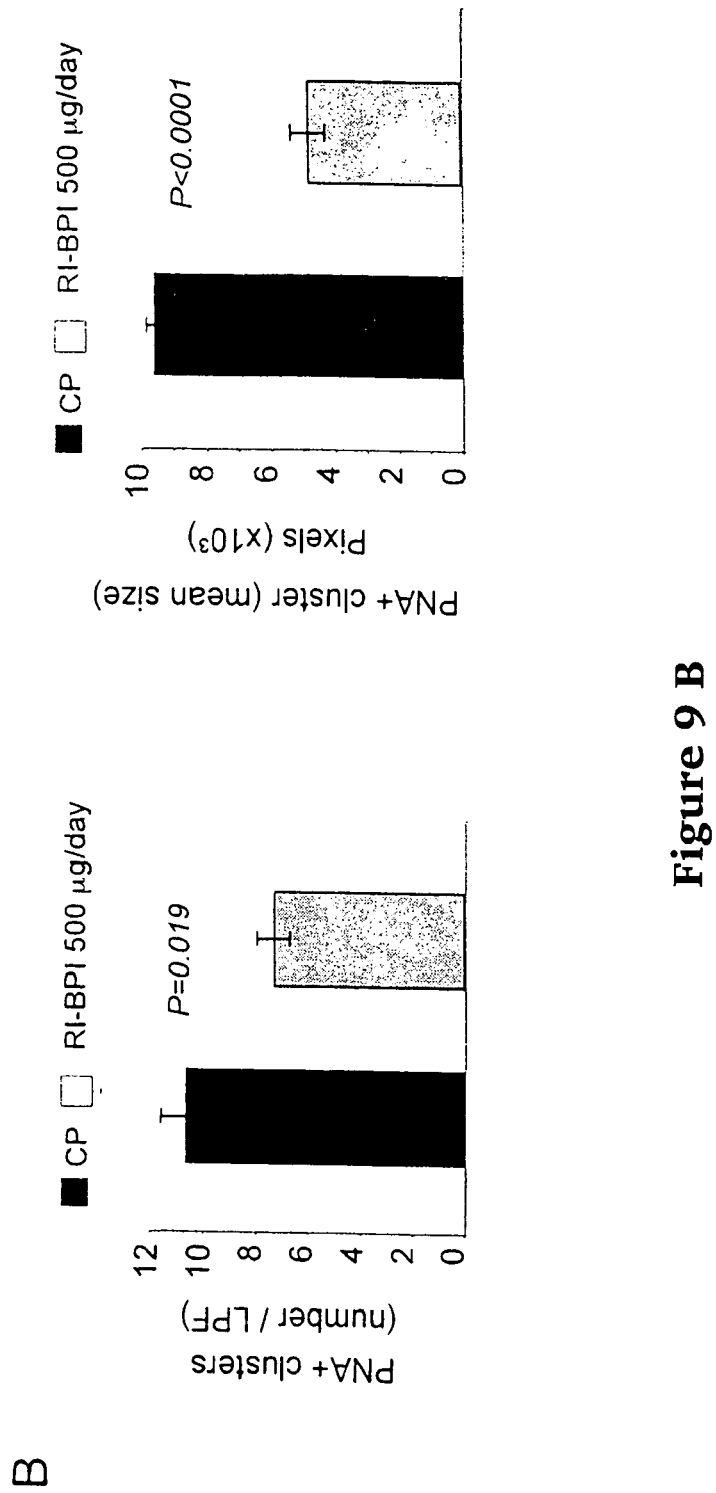
Figure 10:
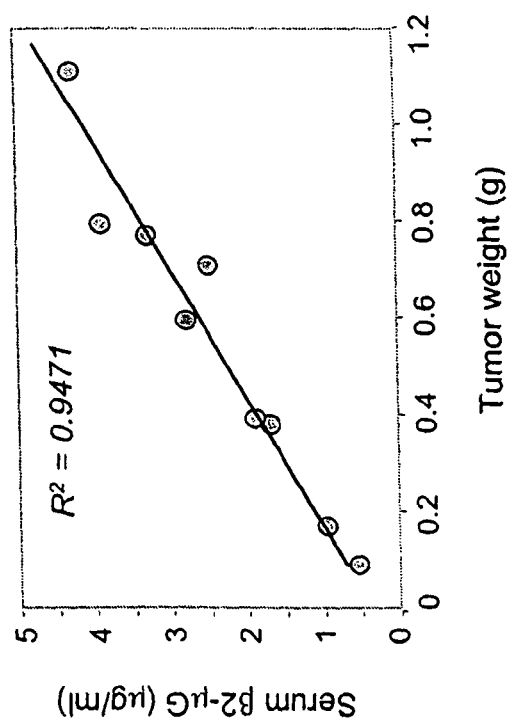
FIG. 10. Human $\beta_2$-microglobulin levels are closely associated with tumor burden in mice baring DLBCL xenografts. Pearson's correlation of serum levels of human $\beta_2$-microglobulin (Y-axis) and tumor burden in grams (X-axis) determined at day 10 in SUDHL4 mice.

Whether the most promising derivative peptide still retained the specific anti-BCL6 properties of the parent recombinant molecule was next validated. The S6.2-BPI was chosen for all subsequent studies since it was the most potent version of retro-inverso BPI (RI-BPI) and was also the easiest to generate on a peptide synthesizer (from hereon, S6.2 is referred to as RI-BPI). In order to determine whether RI-BPI could still bind to BCL6, co-immunoprecipitations between BCL6 and a biotinylated form of RI-BPI was performed. BCL6 polyclonal antibody or an IgG control were used to capture BCL6 from lysates of Ly1 cells exposed to RI-BPI$^{biotin}$ followed by SDS-PAGE and immunodetection using avidin-HRP conjugates (FIG. 1A). BCL6 readily captured RI-BPI indicating that this peptide retained the ability to bind to its target. It was previously shown that BPI specifically blocks the repressor activity of the BCL6 BTB domain but not that of other related transcriptional repressors[13]. Likewise, RI-BPI could specifically inhibit, in a dose-depend fashion, the repressor activity of the BCL6 BTB domain but did not affect the repressor activity of the BTB domains from the Kaiso, HIC1 (hypermethylated in cancer 1) or PLZF (promyelocytic zinc finger) proteins (FIG. 1B). The mechanism of action of BPI consists of occupying the lateral groove of the BCL6 BTB domain, thus impeding recruitment of the SMRT and N-CoR corepressors to BCL6 target genes[13]. Chromatin immunoprecipitations in Ly1 cells exposed to RI-BPI were performed and showed that the peptide was able to exclude SMRT and N-CoR from the BCL6 repression complex that forms on the p53 promoter, but did not affect the binding of BCL6 (FIG. 1C). In accordance with these results, RI-BPI could reactivate the important BCL6 target genes ATR and TP53 in BCL6-dependent DLBCL cells (Ly7, Ly10 and Ly1) but had no effect on Ly4 DLBCL cells (FIG. 1D). BCL6 is required for formation of germinal centers in response to T-cell dependent antigens [1,2]. It was previously shown that recombinant BPI could attenuate formation of germinal centers when administered to immunized mice [13]. To determine whether RI-BPI could also block the activity of BCL6 in vivo, 500 µg of RI-BPI or control peptide was administered intraperitoneally after inducing a T-cell immune response in C57/BL6 mice (n=5 per group). This dose was selected based on the GI$_{50}$ of DLBCL cells, which was previously shown to be similar in sensitivity to BPI as primary centroblasts[3]. After 7 days of injections, the animals were sacrificed and examined for formation of germinal centers within lymphoid follicles by peanut agglutinin staining. The architecture of lymphoid tissue and follicles was identical in RI-BPI and control peptide treated animals, indicating that there was no general toxicity to the lymphoid organs. However, formation of germinal centers was significantly reduced in RI-BPI exposed animals (FIG. 9). Taken together these data indicate that RI-BPI is a specific inhibitor of BCL6 mediated transcriptional repression that can inhibit the biological effects of BCL6 in vivo.

RI-BPI Selectively Kills BCR-Type DLBCL Cells.

A comprehensive unsupervised clustering analysis of a large cohort of DLBCL patients indicated the existence of two cell B-cell autonomous gene expression signatures [19]. DLBCL cells featuring a B-cell receptor (BCR) activation signature expressed BCL6 and were selectively sensitive to BPI, while DLBCL cells with an oxidative phosphorylation (OxPhos) signature were resistant to BPI, regardless of whether they expressed BCL6[16]. Accordingly, it was found that the BCR-type DLBCL cell lines SUDHL4, SUDHL6, Ly1, Ly7, Ly10, Ly3 and Farage (identified through a weighted voting meta-classification scheme published in [16]) were all sensitive to RI-BPI, while the OxPhos cell lines Toledo, Karpas422, Pfeiffer, and Ly4 were resistant (the difference between GI$_{50}$ in sensitive vs. resistant cells is statistically significant, p<0.001, FIG. 2). Like the original full-length form of BPI, RI-BPI retains specific activity against the BCL6 dependent BCR-type DLBCL cells.

RI-BPI Displays Superior Serum and Tissue Permanence.

Figure 3:
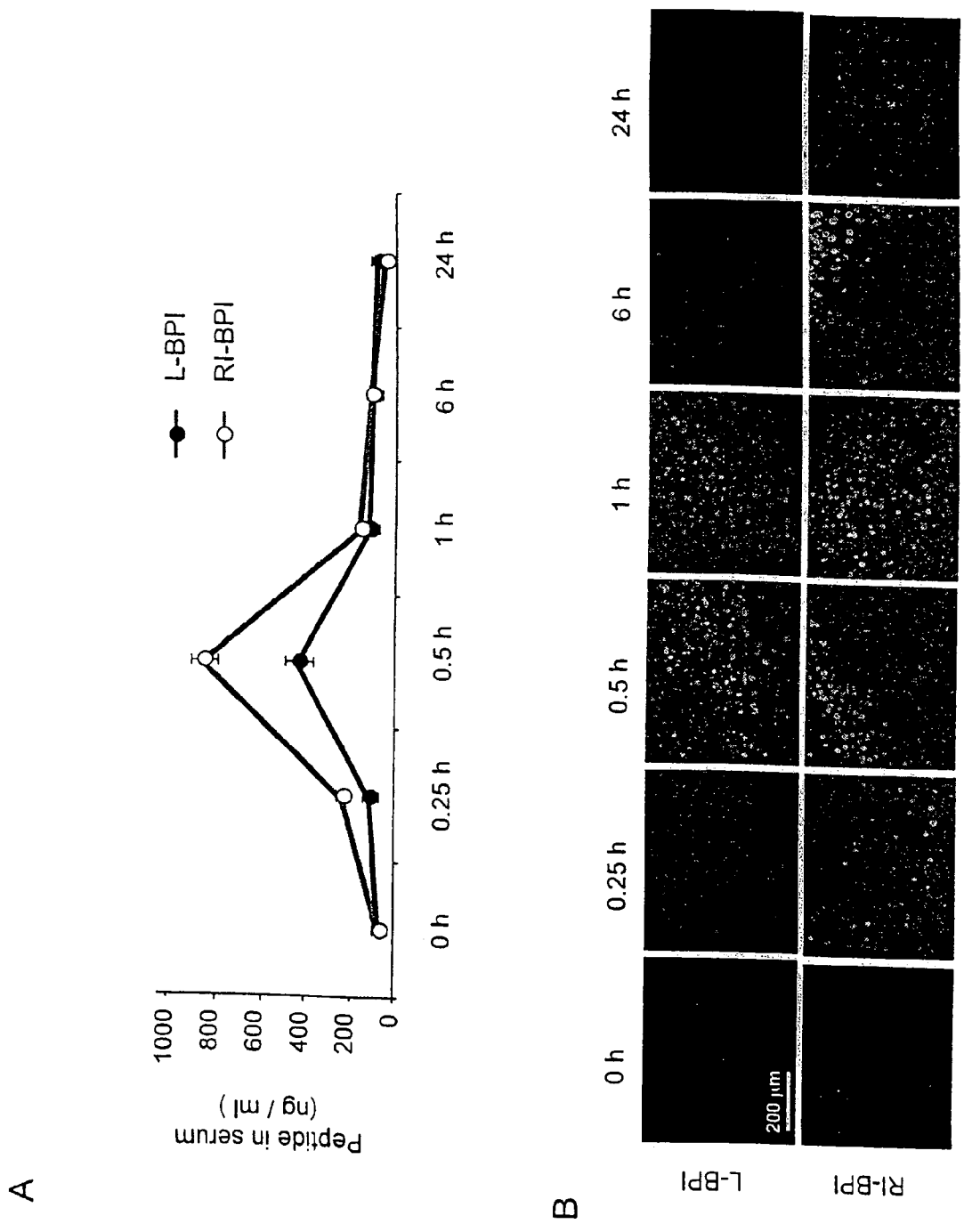
FIGS. 3A-3B. RI-BPI effectively distributes to lymphomas after parenteral administration. A: The serum concentration of RI-BPI$^{biotin}$ and L-BPI$^{biotin}$ was determined after the intraperitoneal administration of 500 μg to mice carrying SUDHL4 xenografts. Serum was taken at several time points (X-axis) and the concentration of biotinylated peptides was determined by chemical reaction with avidin-HRP (Y-axis). B: Histochemistry of the SUDHL4 xenografts injected with RI-BPI$^{biotin}$ and L-BPI$^{biotin}$ performed at similar timepoints as (A). The presence of peptide was detected using Texas red-avidin conjugates followed by fluorescence microscopy.

In order to test whether RI-BPI could perform as an anti-lymphoma therapeutic agent in vivo, whether RI-BPI could penetrate tumor cells after parenteral administration through a distal site, and whether it was more stable in vivo than L-BPI was examined. For this purpose 10$^7$ Ly1 cells were injected into the right flank of 12 SCID mice and allowed to form tumors. Once tumors reached about 1 gram, animals were injected with a single dose of 500 µg of biotinylated RI-BPI or biotinylated S3 L-BPI and sacrificed at 0, 0.25, 0.5, 1, 6 and 24 hours after peptide administration. An avidin-based ELISA assay of serum peptide levels showed that both L-BPI and RI-BPI levels peaked 30 minutes after intraperitoneal injection (FIG. 3A). However, the peak concentration of RI-BPI was double that of L-BPI (43.8±2 ng/ml vs. 20.9±2.5 ng/ml, p>0.001), possibly reflecting the fact that D-peptides are resistant to serum proteases. RI-BPI also reached a higher peak at the 0.25-hour timepoint. Histochemistry of tumors at the same timepoints showed that RI-BPI penetrated tumors more rapidly and persisted longer than L-BPI (FIG. 3B). Peak concentrations in tissue of L-BPI occurred within 30-60 minutes, while in contrast RI-BPI was present at equivalent levels between 60 minutes and 6 hours, and was still detectable in tumor cells 24 hours after administration (FIG. 3B). Although this method of detection is indirect, taking into account the consistence in serum and tissues parameters between this and previous reports, as well as the differences seen between L-BPI and RI-BPI, it is confident that the biotin detected in tissues is peptide-bound biotin rather than free-biotin. Therefore, RI-BPI reached higher serum levels and had a greater duration of tumor tissue residence, suggesting that RI-BPI would be a superior drug-like molecule for pre-clinical trials of anti-lymphoma targeted therapy.

RI-BPI Effectively Suppresses Lymphoma Growth In Vivo.

Figure 4:
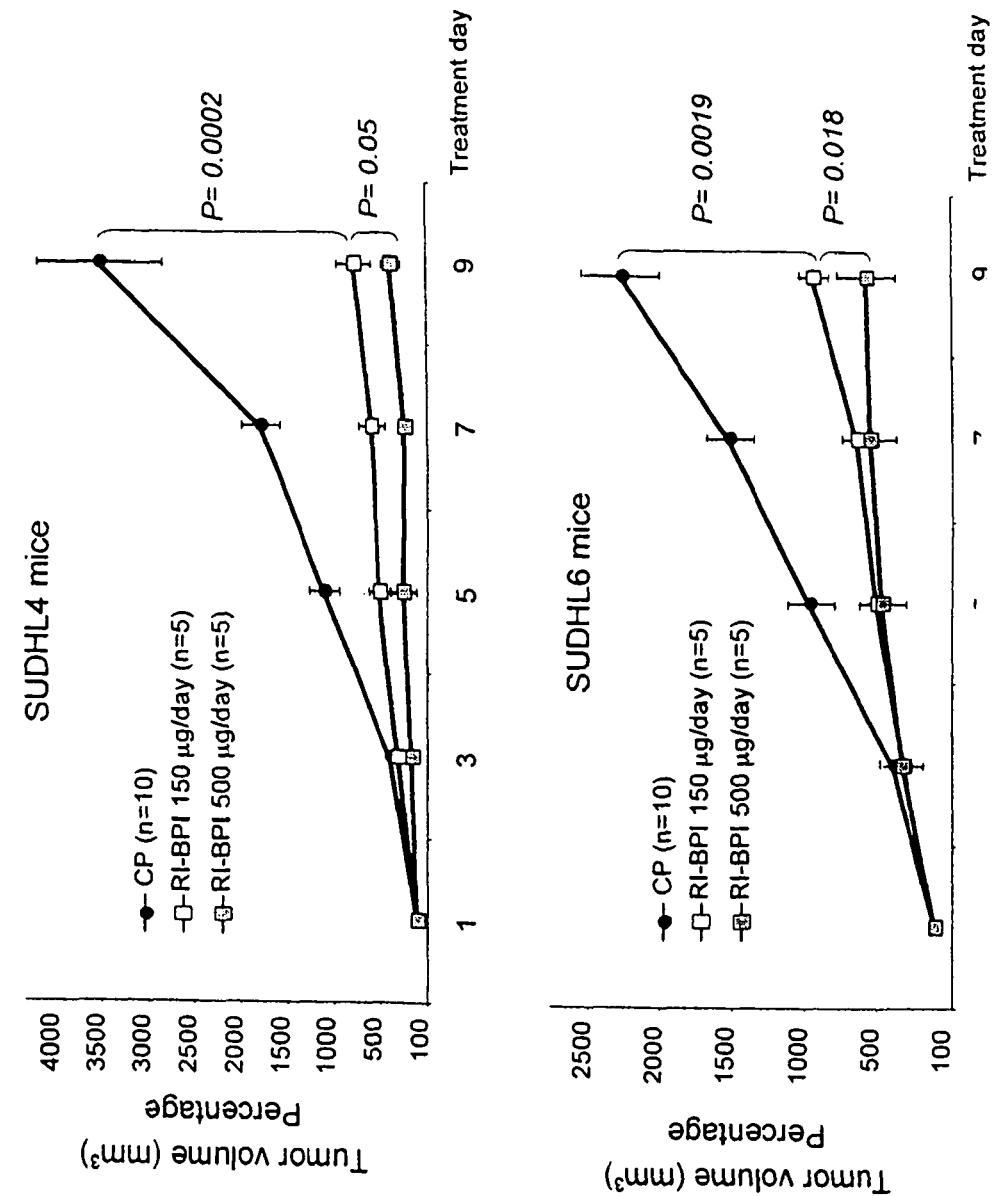
FIGS. 4A-4D. RI-BPI has anti-lymphoma activity in vivo. A: Tumor growth plots in SUDHL4 and SUDHL6 xenografted mice treated with control (black circles) or RI-BPI at 150 μg/day (white squares) or at 500 μg/day (grey squares) for 10 consecutive days. The control peptide group includes mice treated with both the 150 and 500 μg/day doses, which were pooled to facilitate visualization. The Y-axis represents the percentage of tumor volume (in mm$^3$) compared to day 1 of treatment and X-axis represents treatment day. B: Tumor burden (in mg) at day 10 in control (black bars), RI-BPI 150 μg/day (white bars) and RI-BPI 500 μg/day (grey bars) treated SUDHL4 and SUDHL6 mice. C: Serum levels of human-$β_2$-microglobulin (measured in μg/ml and expressed as percentage to their respective controls) at day 10 in control (black bars), RI-BPI 150 μg/day (white bars) and RI-BPI 500 μg/day (grey bars) treated SUDHL4 and SUDHL6 mice. D: Kaplan-Meier survival curves for the pooled mice treated with control (black line), 150 μg/day (blue line) and RI-BPI 500 μg/day (red line). A positive event was pre-analysis defined as either dead of the animal or tumor equal to 10 times the initial volume, whatever occurs first.
Figure 6:
FIGS. 6A-6D. RI-BPI has no anti-lymphoma activity in the Toledo xenograft. A: Tumor growth plot in Toledo (an OxPhos-type cell line) xenografted mice treated with control peptide (black circles) or RI-BPI 500 μg/day (grey squares) for 10 consecutive days. The Y-axis represents the percentage of tumor volume (in mm$^3$) compared to day 1 of treatment and X-axis represents treatment day. B: Tumor burden (in mg) at day 10 in control peptide (black bars) and RI-BPI 500 μg/day (grey bars) treated Toledo mice. C: Serum levels of human-$β_2$-microglobulin (in μg/ml) at day 10 in control peptide (black bars) and RI-BPI 500 μg/day (grey bars)-treated Toledo mice. D: Representative images from Toledo mice tumors after being treated with control peptide (first column) or RI-BPI 500 μg/day (second column), and assayed for apoptosis by TUNEL. The plot on the far right represents the apoptotic index (apoptotic cells over total cells) with the percentage of apoptotic cells in the Y-axis for control peptide (black bars) and RI-BPI 500 μg/day (grey bars).

In order to evaluate the anti-lymphoma activity of BPI, a preclinical study was performed in which two BCR DLBCL cell lines (SUDHL4 and SUDHL6) were each injected into the right flank of 20 SCID mice and allowed to form tumors. Once palpable tumors were detected, pairs of mice were randomized to receive either 150 µg (n=5) or 500 µg (n=5) per day of RI-BPI or control peptide (n=10). All the animals were sacrificed when two or more of the controls had reached the maximal tumor burden permitted by the Albert Einstein Institute for Animal Studies. In addition, one OxPhos cell line (Toledo) was also implanted in SCID mice (n=8) and treated with the 500 µg dose of RI-BPI or similar doses of control peptide as a negative control. Both the size and weight of tumors from RI-BPI treated animals was markedly reduced in a dose dependent manner in both BCR cell lines, but not in the OxPhos tumors (FIG. 4A and FIG. 6A). The tumors in SUDHL4 and SUDHL6 mice were significantly smaller than their respective control at both dose levels (p=0.0002 and p=0.0019 for RI-BPI 150 μg respectively, and p>0.0001 and p=0.0002 for RI-BPI 500 μg respectively) (FIG. 4A). The effect was dose dependent since 500 μg of RI-BPI more profoundly suppressed tumor growth than the 150 μg dose in both cell lines (SUDHL4 p=0.05 and SUDHL6 p=0.018) (FIG. 4A). The tumor mass was also significantly reduced in a dose dependent manner by RI-BPI (FIG. 4B). At the moment of establishing the mouse xenotransplant models of human DLBCL, we found that the levels of human β2 microglobulin in mouse serum were closely correlated (r>0.90) with tumor mass for all the cell lines tested including SUDHL4 (FIG. 11), SUDHL6 and Toledo cells. The levels of serum human $β_2$ microglobulin by ELISA were significantly reduced by BPI in the xenograft experiments as compared to their respective controls (FIG. 4C). Using tumor growth to critical mass (10× from the initial mass) as a surrogate for survival, both the 150 μg (n=10) and the 500 μg (n=10) doses of RI-BPI increased the survival compared to control (n=20) (FIG. 4D, Kaplan-Meier survival curve, Gehan-Wilcoxon test p<0.0001 for multiple samples and Cox's F test p=0.0001 and p=0.05 for RI-BPI 150 μg vs. control, and RI-BPI 150 μg vs. RI-BPI 500 μg respectively). There was no difference in tumor mass, tumor volume and human β2 microglobulin in serum RI-BPI 500 μg and control treated tumors for the Toledo cell xenografts (FIG. 6).

Figure 5:
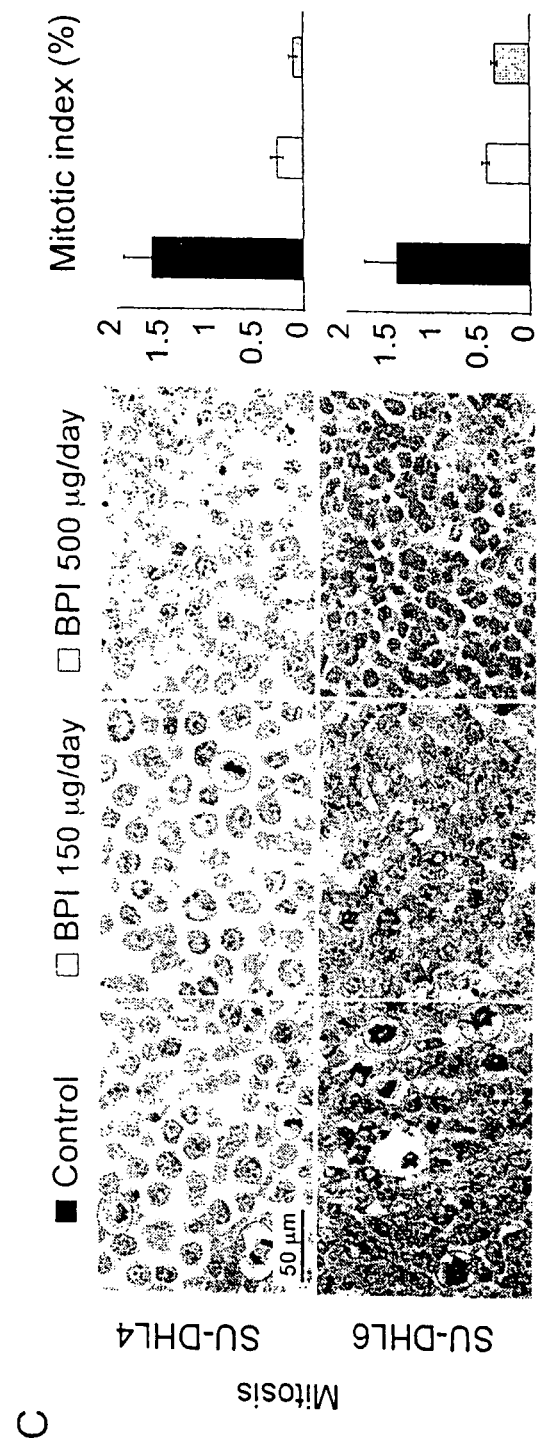
FIGS. 5A-5D. RI-BPI inhibits BCL6 transcriptional repression and induces DLBCL apoptosis in vivo. A: Representative images from SUDHL4 and SUDHL6 mice tumors after being treated with control peptide (first column), RI-BPI 150 μg/day (second column) or RI-BPI 500 μg/day (third column), and assayed for apoptosis by TUNEL. The plot on the far right represents the apoptotic index (apoptotic cells over total cells) with the percentage of apoptotic cells in the Y-axis for pooled control peptide doses (black bars), RI-BPI 150 μg/day (white bars) and RI-BPI 500 μg/day (grey bars) in the X-axis. B: The same tumors as in panel A were assayed for proliferation by PCNA immunostaining. Nuclei were classified as negative, low-intensity positive and high-intensity positive as showed in the inset (digital zoom) of the SUDHL4 control tumor, by green, yellow or red circles respectively. The plot on the far right represents the proliferation index (using the same color coding for negative and positive cells) with the percentage of proliferating and non-proliferating cells in the Y-axis for pooled control peptide samples (first stacking column), RI-BPI 150 μg/day (second stacking column), and RI-BPI 500 μg/day (third stacking column). C: The same tumors were examined for the presence of mitotic cells. The plot on the far right represents the mitotic index (mitotic cells over total cells) with the percentage of mitotic cells in the Y-axis in pooled control peptide samples (black bars), RI-BPI 150 μg/day (white bars) and RI-BPI 500 μg/day (grey bars). D: The mRNA abundance of p53 and ATR was determined in the same tumors as above by quantitative RT-PCR. The Y-axis represents normalized amount of mRNA in arbitrary units as measured by the relative standard curve method.
Figure 5:
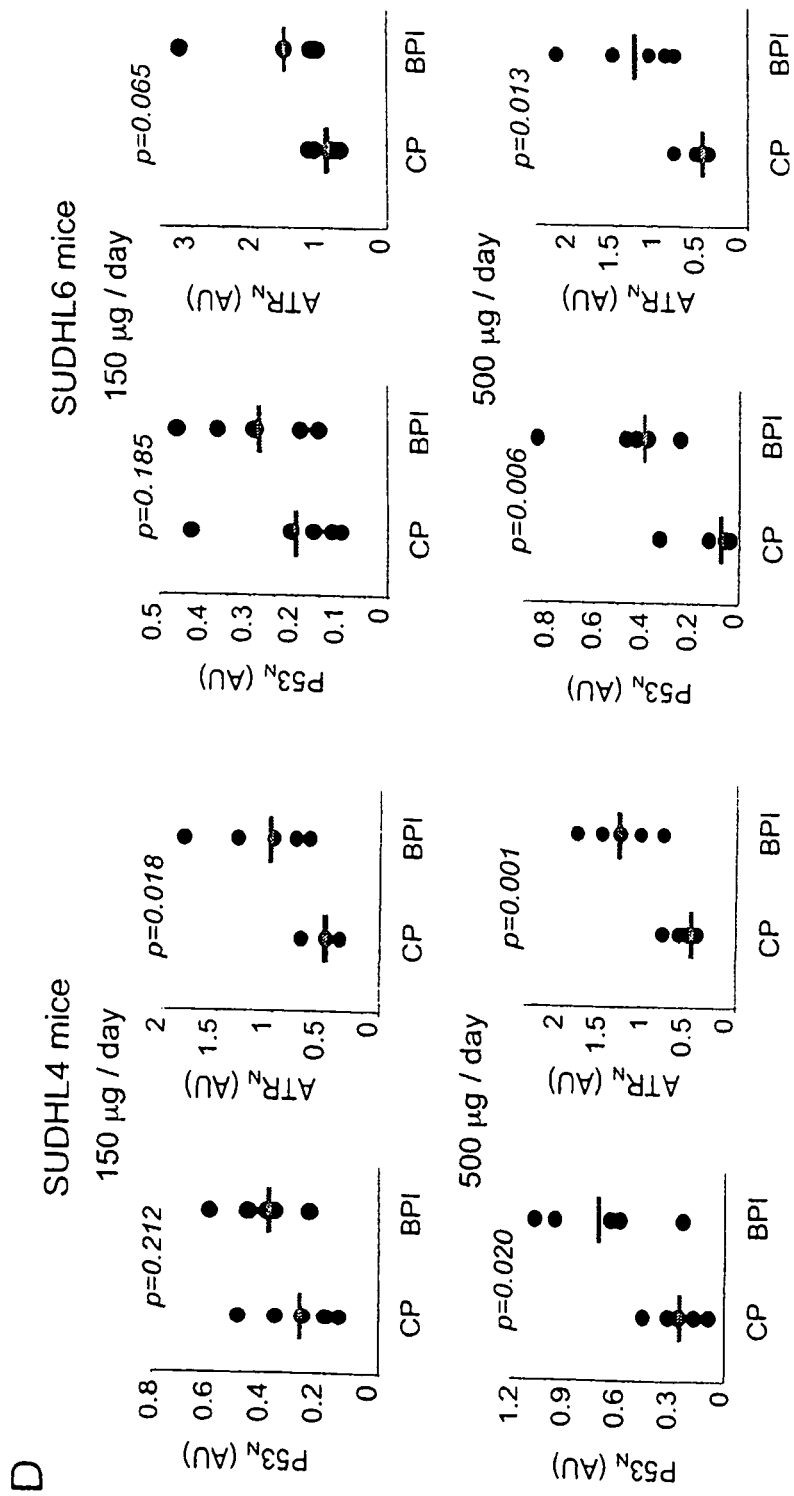

Histological examination of tumors revealed an increased fraction of cells undergoing apoptosis (by TUNEL assay) in RI-BPI treated animals (FIG. 5A). SUDHL4 xenografts treated with control exhibited 1.4±1% apoptosis compared to 13.6±1% and 18.4±1.2% of RI-BPI 150 μg (p<0.001) and 500 μg (p<0.001) treated mice, respectively. SUDHL6 xenografts treated with control exhibited 0.81±0.04% apoptosis compared to 3.8±0.02% and 6.8±2.4% of RI-BPI 150 μg (p<0.001) and 500 μg (p<0.001) treated mice, respectively. There was no difference in apoptosis between RI-BPI and control treated tumors for the Toledo cell xenografts (FIG. 6D). The proliferative index measured as percent of cells staining for PCNA by immunohistochemistry was also significantly decreased (FIG. 5B). SUDHL4 xenografts treated with control presented 29.6±6.4% non-proliferating cells compared to 75.2±3.12% and 78.2±2.2% of RI-BPI 150 μg (p<0.001) and 500 μg (p<0.001) treated mice, respectively. SUDHL6 xenografts treated with control showed 40±3.5% non-proliferating cells compared to 66±2.3% and 65.6±4.8% of RI-BPI 150 μg (p<0.001) and 500 μg (p<0.001) treated mice, respectively. In concordance with these results, the mitotic index of RI-BPI treated xenografts was also significantly reduced (FIG. 5C). RI-BPI mediates its effects by overcoming BCL6 mediated transcriptional repression. In order to determine whether RI-BPI can induce expression of key BCL6 target genes in tumor xenografts, the mRNA abundance of TP53 and ATR was measured by QPCR. RI-BPI induced both genes in a dose dependent manner in DLBCL xenografts (FIG. 5D). Taken together, these data indicate that therapeutic targeting of BCL6 with RI-BPI is an effective anti-lymphoma strategy in vivo.

Figure 11:
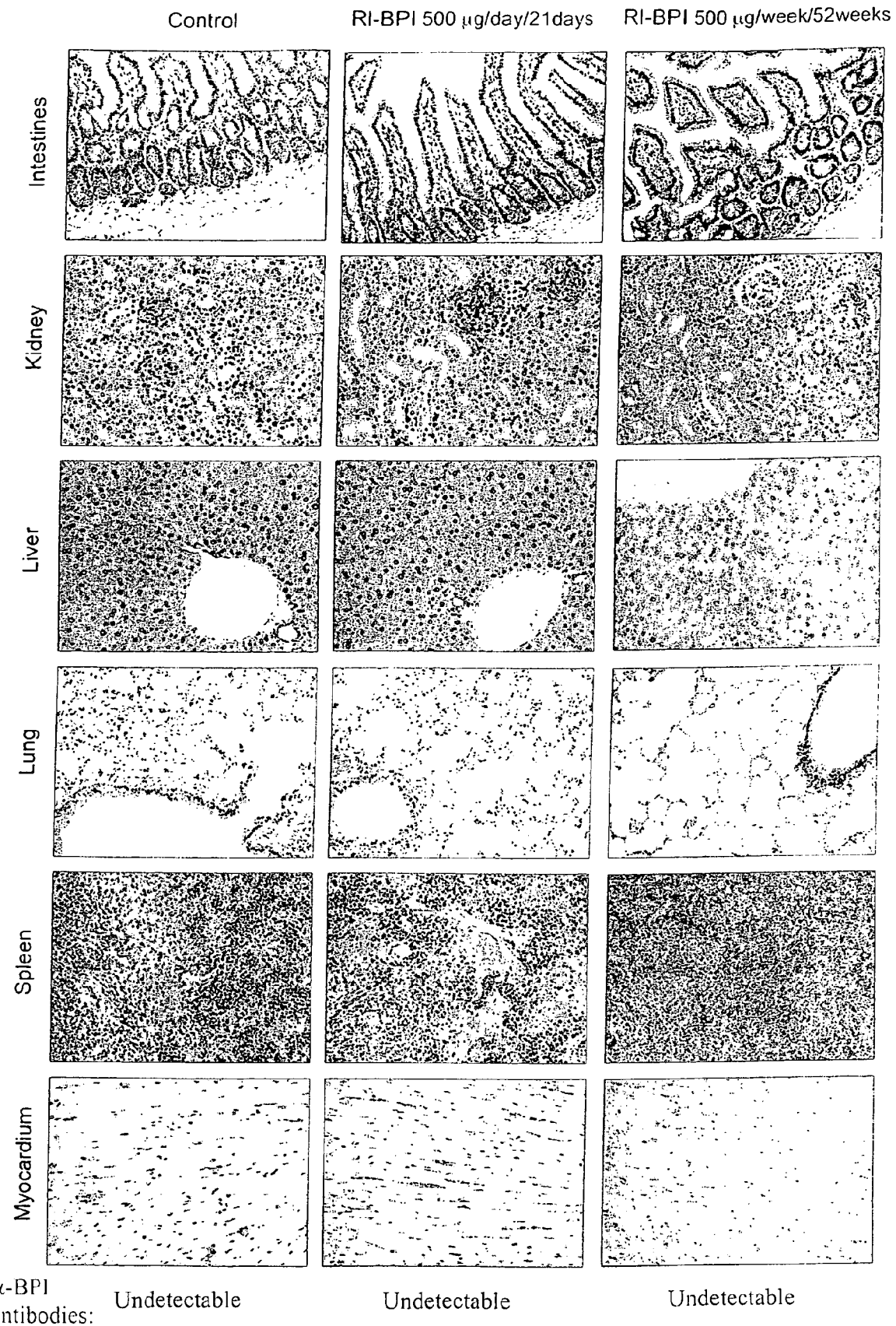
FIG. 11. RI-BPI is non-toxic in mice exposed for periods up to 52 weeks. Representative images of hematoxilin-eosin stained tissues harvested from mice treated with control peptide (first column), RI-BPI 500 µg/day×21 days (second column) and RI-BPI 500 µg/week×52 weeks (third column). Anti-RI-BPI antibodies were not detected in the serum of these mice.

RI-BPI does not induce toxicity or immunogenicity. In order to determine whether RI-BPI could induce toxicity in vivo, a cohort of mice (n=13) were exposed to intraperitoneal injections of 500 μg RI-BPI daily for 21 days (n=5) or to 500 μg RI-BPI weekly for 52 weeks (n=3). None of the animals exhibited signs of weight loss, failure to thrive, or illness, and none of the animals died. Histological examination of tissues including intestines, kidney, liver, lung, spleen, and myocardium revealed normal architecture and cellular composition, comparable to normal controls (FIG. 11). Whether this apparent lack of toxicity could be due to the development of antibodies against the peptides was examined. Serum was collected from all mice treated at both the 21-day and 52-week time courses and examined by ELISA for antibodies immunoreactive to RI-BPI (data not shown). None of the mice developed antibodies able to bind to RI-BPI. Therefore, administration of RI-BPI in a mammalian model organism was safe and non-immunogenic even after prolonged exposure.

RI-BPI can Specifically Kill Primary Human DLBCL Cells.

Figure 7:
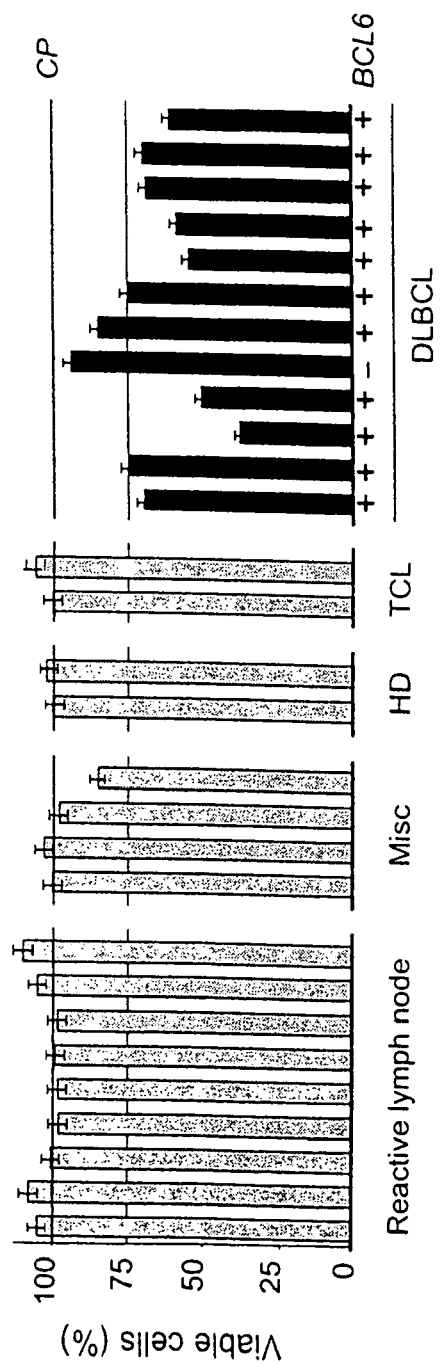
FIG. 7. RI-BPI inhibits the growth of primary human DLBCLs. Single cell suspensions were obtained from lymph node biopsies of patients suspected of having DLBCL and were treated with either BPI 10 μM (bars) or CP 10 μM (line). The grey bars are non-DLBCL samples and the black bars are DLBCLs. The Y-axis represents the percent of viable cells compared to control peptide, which is represented by the line at 100%. Error bars represent the SEM for triplicates. BCL6 status as assessed by immunohistochemistry is shown on the bottom for each DLBCL case. HD: Hodgkin Disease. TCL: T-cell lymphoma. Misc: miscellaneous diagnosis.

Since RI-BPI is a candidate molecule for the treatment of human lymphomas, whether primary DLBCLs could also respond to this drug was examined. Single cell suspensions were obtained from 29 diagnostic lymph node biopsy specimens and exposed to 10 μM RI-BPI or control peptide for 48 hours (FIG. 7). For a majority of the cases, the diagnosis associated with the samples was blinded to the experimentalist. The impact of RI-BPI on viability of these specimens was determined by metabolic labeling in quadruplicate. Nine cases were diagnosed as non-malignant reactive lymph nodes and were not affected by RI-BPI. Two cases each of T-cell lymphoma and Hodgkin's disease were also insensitive to RI-BPI. A miscellaneous group consisting of one head and neck squamous cell carcinoma, one marginal zone lymphoma, one chronic lymphocytic leukemia and one thyroid carcinoma were also unresponsive. Among the twelve DLBCLs, ten cases were positive for BCL6 expression by immunohistochemistry. 9/11 BCL positive cases displayed greater than 25% loss of viability in response to RI-BPI. The one BCL6 negative DLBCL case was not affected by RI-BPI. Therefore, most BCL6 positive human primary DLBCL samples were responsive to RI-BPI.

Discussion

As the most commonly involved oncogene in DLBCL, BCL6 is a potential therapeutic target. The facts that constitutive expression of BCL6 in animals causes DLBCL and that BCL6 loss of function can kill lymphoma cells support this notion[3,4,10,11,13]. Like many transcriptional repressors, BCL6 mediates its actions indirectly, via protein-protein interactions with corepressor complexes that carry out the enzymatic activity of gene silencing. The BTB domain of BCL6 plays a critical role in this process by recruiting the SMRT and N-CoR corepressors to a lateral groove motif formed through homodimerization of BCL6 molecules[12]. The amino acids that line the lateral groove of the BCL6 BTB homodimer make extensive contact with the BBD motif present in SMRT and N-CoR[12]. These residues are unique to BCL6 and are not conserved on other members of the BTB-zinc finger family of transcription factors[12]. The extensive nature of the interface between the BCL6 lateral groove and BBD motif may underlie the higher affinity for SMRT and N-CoR and greater repressor activity of BCL6 vs. other BTB proteins[12,20]; and explain why BPI peptides do not inhibit other BTB domain containing transcriptional repressors ([13] and FIG. 1).

A 120 amino acid recombinant peptide containing the SMRT BBD, a TAT peptide transduction domain and other motifs for purification and immunodetection could specifically inhibit the transcriptional repressor activity of BCL6 and kill DLBCL cells in vitro [13]. Although useful as a proof of principle, this form of BPI required frequent replenishment in tissue culture experiments and frequent dosage in vivo in order to induce biologically significant BCL6 inhibition[13].

In order to generate a more drug-like BCL6 inhibitor comparable to other biologically targeted drugs, the structure of BPI was modified through a series of rationally designed steps. The amount of BBD sequence was reduced to include only the 9 residues that make most extensive contact with the lateral groove. These residues form a macrocyclic structure that inserts deep within the lateral groove and makes multiple physical contacts with the two BTB monomers forming the walls of the groove [12]. One barrier towards efficacy of TAT-delivered peptides is their tendency to become trapped within endosomes after macropinocytosis[15]. In order to enhance endosomal release, a fusogenic motif derived from influenza virus was added, which can disrupt endosomal membranes as they become naturally acidified and thus facilitate release of peptides contained within into the cytoplasm. The influenza fusogenic motif was equally functional in trans or in cis when incorporated into the TAT-BBD peptide. Since recombinant BPI was readily degraded within cells, it needed to be continuously refreshed in the culture medium in order to observe its biological activity[13]. An eleven micromolar dose was required to be administered every four hours in order to reach a median $GI_{50}$ level of 11 μM in vitro at 48 hours. Retro-inverso peptides generated with D-amino acids are resistant to most proteases and can retain the proper secondary structural orientation needed for their activity. A single dose of D-retroinverso TAT-BBD-fusogenic form of BPI was equally potent as the original recombinant BPI given every four hours. The 16 micromolar dose is in a similar range as other biologically active drugs such as SAHA[21], lenalidomide[22] and the Syk kinase inhibitor R406 (syk inhibitor) [23].

From the pharmacodynamic standpoint, RI-BPI could disrupt endogenous BCL6 repression complexes and reactivate critical target genes such as the ATR and TP53 cellular checkpoint mediators. In a phenocopy of BCL6 deficient mice, RI-BPI inhibited the formation of germinal centers in the secondary lymphoid organs. Previous studies showed that BCL6 mediates survival of primary germinal center B cells and DLBCL cells in a SMRT and N-CoR dependent manner [3,13,24]. In contrast, other actions of BCL6 such as differentiation blockade and negative autoregulation are dependent on different corepressors such as MTA3 and CtBP that do not interact with BCL6 through the lateral groove [13,24,25,26]. Inhibition of the BCL6 lateral groove by BPI or RI-BPI does not affect these other BCL6 activities ([13,24,26] and data not shown). It seems likely that the severe inflammatory response observed in BCL6-null mice, which is mostly due to loss of BCL6 function in T-cells[27] is also mediated through a different biochemical mechanism, since this biological effect was not observed in immunocompetent mice treated with RI-BPI for up to one year (Supp FIG. 5). In fact, there was no evidence of toxicity in animals exposed to BPI for up to one year, raising the possibility that this form of targeted transcription therapy causing a partial rather than total loss of function of BCL6 could selectively inhibit the principle lymphomagenic effects of BCL6 without affecting many of its other biological activities and thus avoiding potential side effects.

Although DLBCLs are a markedly heterogeneous group of tumors from the molecular standpoint, they can be grouped into biologically meaningful subtypes by examining their gene expression profiles. One such approach based on three different unbiased clustering methods could separate DLBCLs into three groups. The most frequent subtype of DLBCL thus identified featured prominent expression of genes involved in B-cell receptor (BCR) signaling and proliferation [19]. The BCR signature was shown to be indicative of DLBCLs that were biologically dependent on BCL6, since they featured coordinated regulation of BCL6 target genes and differential sensitivity to BCL6 blockade [16]. Accordingly, RI-BPI was also selectively active against the BCR DLBCL cell lines SUDHL4, SUDHL6, Ly1, Ly3, Ly7, Ly10 and Farage but not the non-BCR DLBCL cell lines Ly4, Toledo, Pfeiffer and Karpas422 (the classification of DLBCL cell lines was reported in [16]). When BCR DLBCL cells were implanted in mice, RI-BPI potently suppressed tumor formation in a dose-dependent manner. This was due both to induction of cell death and growth arrest and was associated with induction of the important BCL6 regulated checkpoint genes ATR and TP53. This was achieved at doses equivalent to 7.5 mg/kg to 25 mg/kg, which is within the dose range of clinically successful protein based drugs such as rituximab. Therefore, xenograft tumors formed from human BCR DLBCL cells remain biologically dependent on BCL6, and can be safely treated by BCL6 targeted therapy. Although gene signature based classification was not possible to obtain from the primary DLBCL patient samples used in our study, a majority of the BCL6 positive DLBCLs were also responsive to BPI, whereas normal human tissue or other types of tumors were not affected by this agent. Finally, RI-BPI exhibited favorable pharmacokinetics, persisting for at least 24 hours in tumors after administered parenterally via distal site, was safe to administer for periods up to one year, and did not induce an immune reaction. Rational design of a peptidomimetic inhibitor of BCL6 demonstrates that this oncoprotein is an excellent therapeutic target for anti-lymphoma targeted therapy and has the potential to benefit patients with DLBCL.

REFERENCES

1. Ye B H, Cattoretti G, Shen Q, Zhang J, Hawe N, et al. (1997) The BCL-6 proto-oncogene controls germinal-centre formation and Th2-type inflammation. Nat Genet 16: 161-170.
2. Dent A L, Shaffer A L, Yu X, Allman D, Staudt L M (1997) Control of inflammation, cytokine expression, and germinal center formation by BCL-6. Science 276: 589-592.
3. Ranuncolo S M, Polo J M, Dierov J, Singer M, Kuo T, et al. (2007) Bcl-6 mediates the germinal center B cell phenotype and lymphomagenesis through transcriptional repression of the DNA-damage sensor ATR. Nat Immunol 8: 705-714.
4. Phan R T, Dalla-Favera R (2004) The BCL6 proto-oncogene suppresses p53 expression in germinal-centre B cells. Nature 432: 635-639.
5. Phan R T, Saito M, Basso K, Niu H, Dalla-Favera R (2005) BCL6 interacts with the transcription factor Miz-1 to suppress the cyclin-dependent kinase inhibitor p21 and cell cycle arrest in germinal center B cells. Nat Immunol 6: 1054-1060.
6. Shaffer A L, Lin K I, Kuo T C, Yu X, Hurt E M, et al. (2002) Blimp-1 orchestrates plasma cell differentiation by extinguishing the mature B cell gene expression program. Immunity 17: 51-62.
7. Tunyaplin C, Shaffer A L, Angelin-Duclos C D, Yu X, Staudt L M, et al. (2004) Direct repression of prdm1 by Bcl-6 inhibits plasmacytic differentiation. J Immunol 173: 1158-1165.
8. Ye B H, Lista F, Lo Coco F, Knowles D M, Offit K, et al. (1993) Alterations of a zinc finger-encoding gene, BCL-6, in diffuse large-cell lymphoma. Science 262: 747-750.

9. Pasqualucci L, Neumeister P, Goossens T, Nanjangud G, Chaganti R S, et al. (2001) Hypermutation of multiple proto-oncogenes in B-cell diffuse large-cell lymphomas. Nature 412: 341-346.
10. Baron B W, Anastasi J, Montag A, Huo D, Baron R M, et al. (2004) The human BCL6 transgene promotes the development of lymphomas in the mouse. Proc Natl Acad Sci USA 101: 14198-14203.
11. Cattoretti G, Pasqualucci L, Ballon G, Tam W, Nandula S V, et al. (2005) Deregulated BCL6 expression recapitulates the pathogenesis of human diffuse large B cell lymphomas in mice. Cancer Cell 7: 445-455.
12. Ahmad K F, Melnick A, Lax S, Bouchard D, Liu J, et al. (2003) Mechanism of SMRT corepressor recruitment by the BCL6 BTB domain. Mol Cell 12: 1551-1564.
13. Polo J M, Dell'Oso T, Ranuncolo S M, Cerchietti L, Beck D, et al. (2004) Specific peptide interference reveals BCL6 transcriptional and oncogenic mechanisms in B-cell lymphoma cells. Nat Med 10: 1329-1335.
14. Wadia J S, Dowdy S F (2005) Transmembrane delivery of protein and peptide drugs by TAT-mediated transduction in the treatment of cancer. Adv Drug Deliv Rev 57: 579-596.
15. Wadia J S, Stan R V, Dowdy S F (2004) Transducible TAT-HA fusogenic peptide enhances escape of TAT-fusion proteins after lipid raft macropinocytosis. Nat Med 10: 310-315.
16. Polo J M, Juszczynski P, Monti S, Cerchietti L, Ye K, et al. (2007) Transcriptional signature with differential expression of BCL6 target genes accurately identifies BCL6-dependent diffuse large B cell lymphomas. Proc Natl Acad Sci USA 104: 3207-3212.
17. Cattoretti G, Shaknovich R, Smith P M, Jack H M, Murty V V, et al. (2006) Stages of germinal center transit are defined by B cell transcription factor coexpression and relative abundance. J Immunol 177: 6930-6939.
18. Snyder E L, Meade B R, Saenz C C, Dowdy S F (2004) Treatment of terminal peritoneal carcinomatosis by a transducible p53-activating peptide. PLoS Biol 2: E36.
19. Monti S, Savage K J, Kutok J L, Feuerhake F, Kurtin P, et al. (2005) Molecular profiling of diffuse large B-cell lymphoma identifies robust subtypes including one characterized by host inflammatory response. Blood 105: 1851-1861.
20. Melnick A, Carlile G, Ahmad K F, Kiang C L, Corcoran C, et al. (2002) Critical residues within the BTB domain of PLZF and Bcl-6 modulate interaction with corepressors. Mol Cell Biol 22: 1804-1818.
21. Sakajiri S, Kumagai T, Kawamata N, Saitoh T, Said J W, et al. (2005) Histone deacetylase inhibitors profoundly decrease proliferation of human lymphoid cancer cell lines. Exp Hematol 33: 53-61.
22. Hernandez-Ilizaliturri F J, Reddy N, Holkova B, Ottman E, Czuczman M S (2005) Immunomodulatory drug CC-5013 or CC-4047 and rituximab enhance antitumor activity in a severe combined immunodeficient mouse lymphoma model. Clin Cancer Res 11: 5984-5992.
23. Chen L, Monti S, Juszczynski P, Daley J, Chen W, et al. (2007) SYK-dependent tonic B-cell receptor signaling is a rational treatment target in diffuse large B-cell lymphoma. Blood.
24. Parekh S, Polo J M, Shaknovich R, Juszczynski P, Lev P, et al. (2007) BCL6 programs lymphoma cells for survival and differentiation through distinct biochemical mechanisms. Blood 110: 2067-2074.
25. Fujita N, Jaye D L, Geigerman C, Akyildiz A, M. R. M, et al. (2004) MTA3 and Mi-2/NuRD Complex Regulate Cell Fate During B-Lymphocyte Differentiation. Cell 119: 75-86.
26. Mendez L, Polo J, Yu J, Kruski M, Ding B, et al. (2008) CtBP is an essential corepressor for BCL6 autoregulation. Mol Cell Biol In Press.
27. Toney L M, Cattoretti G, Graf J A, Merghoub T, Pandolfi P P, et al. (2000) BCL-6 regulates chemokine gene transcription in macrophages. Nat Immunol 1: 214-220.

---

What is claimed is:

1. A compound that binds to a BCL6 lateral groove and prevents binding of a corepressor to the lateral groove, wherein the compound comprises a peptide or mimetic consisting of the amino acid sequence GRGIEHISR (SEQ ID NO:1) or the amino acid sequence GRGIEHISRG (SEQ ID NO:2).

2. The compound of claim 1, wherein the peptide or mimetic consists of the amino acid sequence GRGIEHISR (SEQ ID NO:1).

3. The compound of claim 1, wherein the peptide or mimetic consists of the amino acid sequence GRGIEHISRG (SEQ ID NO:2).

4. The compound of claim 1, wherein the compound further comprises a TAT sequence and a fusogenic sequence having the amino acid sequence NH$_2$-GLFGAIAGFIENG-WEGMIDG-OH (SEQ ID NO:8).

5. The compound of claim 4, wherein the peptide or mimetic is directly linked to the TAT sequence, and the TAT sequence is directly linked to the fusogenic sequence.

6. The compound of claim 4, wherein the TAT sequence is directly linked to the peptide or mimetic, and the peptide or mimetic is directly linked to the fusogenic sequence.

7. The compound of claim 4, wherein the TAT sequence is directly linked to the fusogenic sequence, and the fusogenic sequence is directly linked to the peptide or mimetic.

8. The compound of claim 1 in a pharmaceutically acceptable excipient.

9. A method for blocking corepressor binding to a BCL6 lateral groove, the method comprising contacting the BCL6 with the compound of claim 1, wherein the BCL6 is in a lymphoma cell or a breast cancer cell.

10. The method of claim 9, wherein the lymphoma cell or breast cancer cell is in a human.

11. The method of claim 9, wherein the cell is a lymphoma cell.

12. The method of claim 9, wherein the cell is a breast cancer cell.

13. A method of inhibiting BCL6 repression in a mammalian cell, method comprising treating the cell with the compound of claim 1, wherein the cell is a lymphoma cell or a breast cancer cell.

14. The method of claim 13, wherein the cell is a lymphoma cell.

15. The method of claim 13, wherein the cell is a breast cancer cell.

16. The method of claim 13, wherein the cell is in a mammal.

17. The method of claim 16, wherein the mammal is a human.

18. A method for treating a mammal with cancer, wherein the cancer requires BCL6 repression, the method comprising administering the compound of claim 8 to the mammal, wherein the cancer is a lymphoma or a breast cancer.

19. The method of claim 18, wherein the mammal is a human.

20. The method of claim 18, wherein the cancer is a lymphoma.

21. The method of claim 18, wherein the cancer is a breast cancer.

22. An isolated polypeptide comprising the amino acid sequence GRGIEHISR (SEQ ID NO:1).

* * * * *

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial
<220> FEATURE:
<223> OTHER INFORMATION: peptide that binds BCL6

<400> SEQUENCE: 1

Gly Arg Gly Ile Glu His Ile Ser Arg
1               5

<210> SEQ ID NO 2
<211> LENGTH: 10
<212> TYPE: PRT
<213> ORGANISM: Artificial
<220> FEATURE:
<223> OTHER INFORMATION: peptide that binds BCL6

<400> SEQUENCE: 2

Gly Arg Gly Ile Glu His Ile Ser Arg Gly
1               5                   10

<210> SEQ ID NO 3
<211> LENGTH: 12
<212> TYPE: PRT
```

```
<213> ORGANISM: Artificial
<220> FEATURE:
<223> OTHER INFORMATION: control peptide for S1 and S2

<400> SEQUENCE: 3

Tyr Gly Arg Lys Lys Arg Arg Gln Arg Arg Gly
1               5                   10

<210> SEQ ID NO 4
<211> LENGTH: 31
<212> TYPE: PRT
<213> ORGANISM: Artificial
<220> FEATURE:
<223> OTHER INFORMATION: control peptide for S3

<400> SEQUENCE: 4

Gly Leu Phe Gly Ala Ile Ala Gly Phe Ile Glu Asn Gly Trp Glu Gly
1               5                   10                  15

Met Ile Asp Gly Gly Arg Lys Lys Arg Arg Gln Arg Arg Gly
            20                  25                  30

<210> SEQ ID NO 5
<211> LENGTH: 31
<212> TYPE: PRT
<213> ORGANISM: Artificial
<220> FEATURE:
<223> OTHER INFORMATION: Control peptide for S4, S5 and S6.  Amino acids
      at positions 2-10, 13-15, 17-18, 20-23, 25-27 and 29-30 are D
      isomers.

<400> SEQUENCE: 5

Gly Arg Arg Arg Gln Arg Arg Lys Lys Arg Gly Gly Asp Ile Met Gly
1               5                   10                  15

Glu Trp Gly Asn Glu Ile Phe Gly Ala Ile Ala Gly Phe Leu Gly
            20                  25                  30

<210> SEQ ID NO 6
<211> LENGTH: 12
<212> TYPE: PRT
<213> ORGANISM: Artificial
<220> FEATURE:
<223> OTHER INFORMATION: Control peptide for S7.  Amino acids at
      positions 2-10 are D isomers.

<400> SEQUENCE: 6

Gly Arg Arg Arg Gln Arg Arg Lys Lys Arg Gly Gly
1               5                   10

<210> SEQ ID NO 7
<211> LENGTH: 12
<212> TYPE: PRT
<213> ORGANISM: Artificial
<220> FEATURE:
<223> OTHER INFORMATION: TAT peptide

<400> SEQUENCE: 7

Tyr Gly Arg Lys Lys Arg Arg Gln Arg Arg Gly
1               5                   10

<210> SEQ ID NO 8
<211> LENGTH: 20
<212> TYPE: PRT
<213> ORGANISM: Artificial
<220> FEATURE:
<223> OTHER INFORMATION: Fusogenic peptide

<400> SEQUENCE: 8
```

```
Gly Leu Phe Gly Ala Ile Ala Gly Phe Ile Glu Asn Gly Trp Glu Gly
1               5                   10                  15

Met Ile Asp Gly
            20

<210> SEQ ID NO 9
<211> LENGTH: 19
<212> TYPE: DNA
<213> ORGANISM: Artificial
<220> FEATURE:
<223> OTHER INFORMATION: primer for p53

<400> SEQUENCE: 9
aatcaaccca cagctgcac                                              19

<210> SEQ ID NO 10
<211> LENGTH: 20
<212> TYPE: DNA
<213> ORGANISM: Artificial
<220> FEATURE:
<223> OTHER INFORMATION: primer for p53

<400> SEQUENCE: 10
tcttctgtcc cttcccagaa                                             20

<210> SEQ ID NO 11
<211> LENGTH: 9
<212> TYPE: PRT
<213> ORGANISM: Artificial
<220> FEATURE:
<223> OTHER INFORMATION: peptide that binds BCL6

<400> SEQUENCE: 11

Gly Arg Ser Ile His Glu Ile Pro Arg
1               5
```